United States Patent
Amano et al.

(10) Patent No.: US 7,585,464 B2
(45) Date of Patent: Sep. 8, 2009

(54) BIOSENSOR CARTRIDGE AND BIOSENSOR DISPENSING DEVICE

(75) Inventors: Yoshinori Amano, Saijo (JP); Toshiaki Iio, Saijo (JP); Kouichi Matsuda, Niihama (JP)

(73) Assignee: Panasonic Corporation, Osaka (JP)

( * ) Notice: Subject to any disclaimer, the term of this patent is extended or adjusted under 35 U.S.C. 154(b) by 812 days.

(21) Appl. No.: 10/510,917

(22) PCT Filed: Apr. 16, 2003

(86) PCT No.: PCT/JP03/04865

§ 371 (c)(1),
(2), (4) Date: Oct. 12, 2004

(87) PCT Pub. No.: WO03/089917

PCT Pub. Date: Oct. 30, 2003

(65) Prior Publication Data

US 2005/0145491 A1 Jul. 7, 2005

(30) Foreign Application Priority Data

Apr. 19, 2002 (JP) .............................. 2002-116902

(51) Int. Cl.
*G01N 27/00* (2006.01)
(52) U.S. Cl. .......................... 422/68.1; 422/61; 422/63; 422/104; 422/58; 436/44; 436/808; 436/150; 436/43; 221/171; 221/208; 204/400; 204/403.01; 204/403.02; 204/407
(58) Field of Classification Search ....................... None
See application file for complete search history.

(56) References Cited

U.S. PATENT DOCUMENTS

| 5,030,418 | A | * | 7/1991 | Miyata ........................ 422/63 |
| 6,151,110 | A | * | 11/2000 | Markart ...................... 356/244 |
| 6,200,442 | B1 | * | 3/2001 | Markart ...................... 204/400 |
| 7,449,148 | B2 | * | 11/2008 | Matsumoto et al. ........... 422/63 |
| 2002/0057993 | A1 | * | 5/2002 | Maisey et al. ............. 422/82.01 |
| 2002/0104849 | A1 | * | 8/2002 | Giruad ....................... 221/270 |
| 2003/0002387 | A1 | * | 1/2003 | Bottwein et al. ............ 366/273 |
| 2003/0089730 | A1 | * | 5/2003 | May et al. .................... 221/232 |

(Continued)

FOREIGN PATENT DOCUMENTS

EP 1 347 296 9/2003

(Continued)

OTHER PUBLICATIONS

Amano et al., JP 2001-281199, May 25, 2001, machine translation from JPO.*

*Primary Examiner*—Jill Warden
*Assistant Examiner*—P. Kathryn Wright
(74) *Attorney, Agent, or Firm*—Steptoe & Johnson LLP

(57) ABSTRACT

A compact biosensor cartridge allows biosensors to be tested one by one and protects the biosensors from moisture until they are set. A biosensor dispensing device is also disclosed. A biosensor cartridge may be installed in the dispensing device and pushing and rotating elements are both used to eject the biosensors through a sensor ejecting port in the case. The biosensors are discharged to outside the case when ejection means inside the cartridge are driven by a driving means outside the biosensor cartridge. This configuration allows the biosensor cartridge to be made smaller and thinner.

27 Claims, 19 Drawing Sheets

U.S. PATENT DOCUMENTS

| | | | |
|---|---|---|---|
| 2003/0116583 A1* | 6/2003 | Pugh | 221/268 |
| 2003/0191415 A1* | 10/2003 | Moerman et al. | 600/584 |
| 2005/0186162 A1* | 8/2005 | Sato | 424/63 |
| 2008/0164280 A1* | 7/2008 | Kuriger et al. | 221/135 |

FOREIGN PATENT DOCUMENTS

| | | |
|---|---|---|
| JP | 3-80353 | 8/1991 |
| JP | 6-294769 | 10/1994 |
| JP | 7-151721 | 6/1995 |
| JP | 7-167819 | 7/1995 |
| JP | 7-167820 | 7/1995 |
| JP | 9-184819 | 7/1997 |
| JP | 9-250998 | 9/1997 |
| JP | 10-253570 | 9/1998 |
| JP | 2000-171427 | 6/2000 |
| JP | 2001-141686 | 5/2001 |
| JP | 2001-281199 | 10/2001 |
| JP | 2003-42994 | 2/2003 |

* cited by examiner

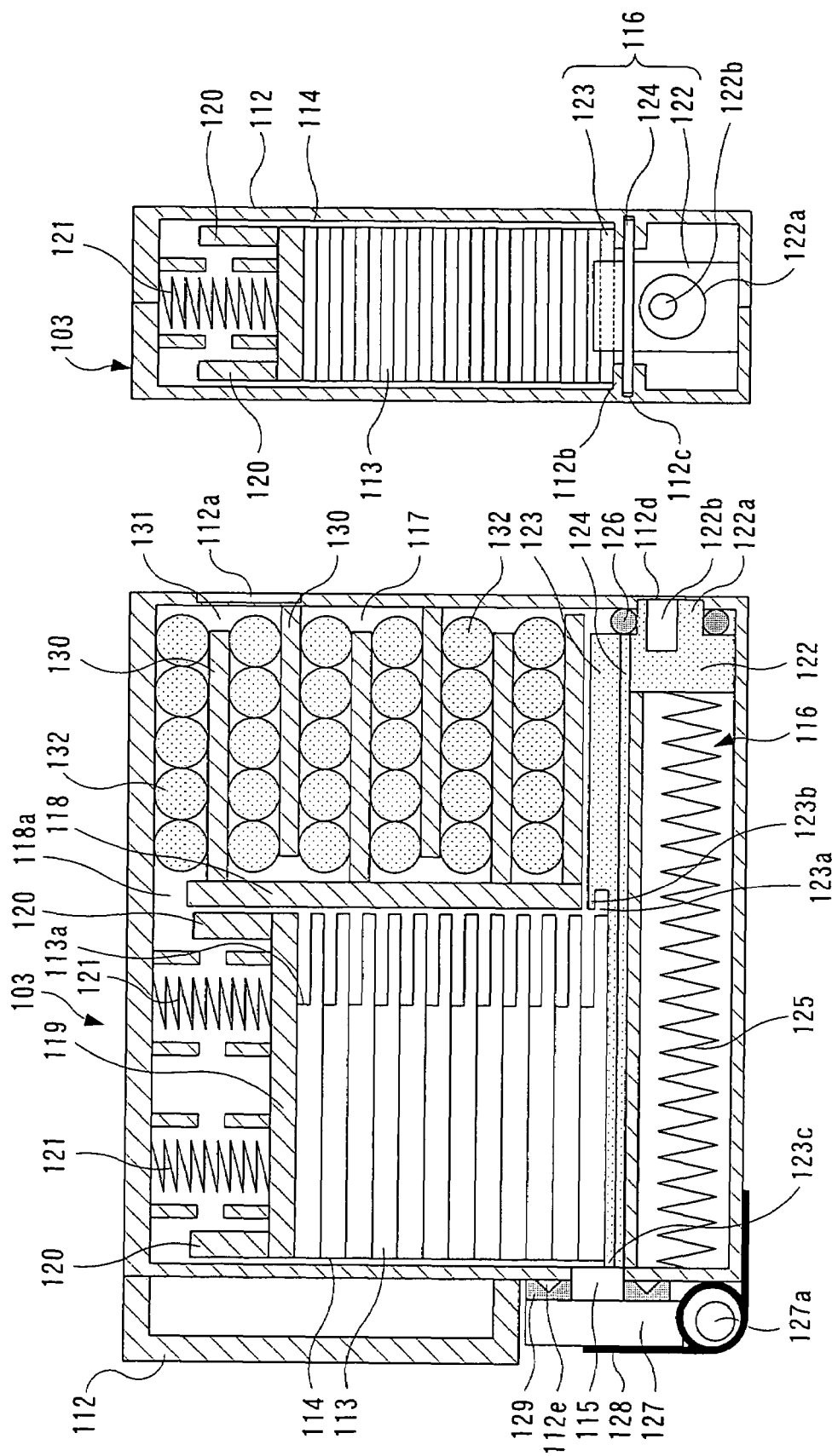

FIG. 19A  PRIOR ART
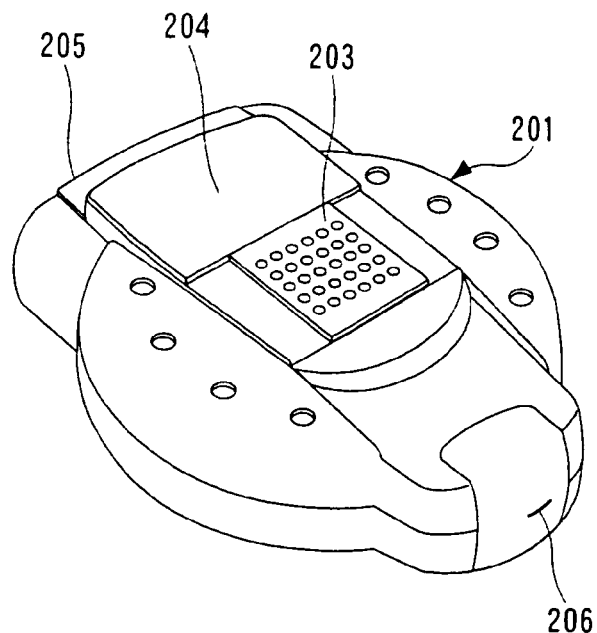
PRIOR ART  FIG. 19B
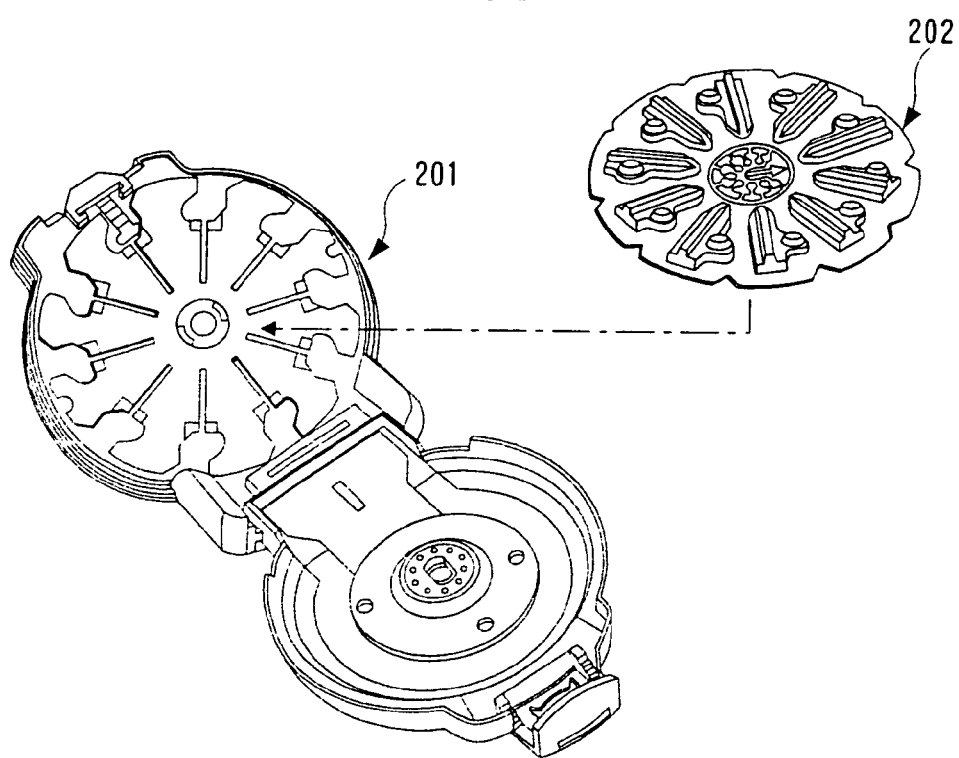

BIOSENSOR CARTRIDGE AND BIOSENSOR DISPENSING DEVICE

TECHNICAL FIELD

The present invention relates to a biosensor cartridge and a biosensor dispensing device for storing a plurality of biosensors for measuring a specific component in a sample and dispensing the biosensor one by one.

BACKGROUND ART

Recently, as various biosensors utilizing a special catalytic action of an enzyme are being developed and being applied to the clinical field, a biosensor for rapidly and accurately testing and determining the quantity of a specific component in a sample is being put to practical use.

Nowadays, a number of diabetic patients are significantly increasing, and regarding glucose, for example, a very complicating procedure of centrifuging blood and measuring plasma as a sample are conventionally required to measure and manage the blood sugar level, and thus a biosensor for measuring a whole blood is desired and is being put to practical use.

Such biosensors include that disclosed in for example, JP-A 61-294351 (1986), in which a predetermined voltage is supplied to an electrode system of a sensor applied with the whole blood, a current value flowing between the electrodes is measured, a glucose concentration in a sample solution is calculated based on the measured value, and the value thereof is displayed on a display unit of a dedicated measuring instrument.

A biosensor dispensing device, in which a sensor pack or a sensor bottle set with a plurality of biosensors is installed in a measuring instrument, for dispensing the biosensors one by one is disclosed. By virtue of such a biosensor dispensing device, even users such as diabetic patients that are mostly elderly are less likely to perform a wrong operation such as accidentally dropping the biosensor when installing, attaching in an opposite direction, or further, performing measurement with the device attached in the opposite direction.

The biosensor dispensing device disclosed in JP-A 8-262026 (1996) includes a substantially circular plate-shaped sensor pack 202 inside a housing 201 formed by attaching an upper case and a lower case in a freely opening and closing manner like a bivalve shell, as shown in FIGS. 19A and 19B. The sensor pack 202 contains a blood-glucose sensor in each of a plurality of sensor holding cavities and is communicated with a desiccant cavity. A sliding latch 203 for operating a sliding actuator is arranged in the upper case, and by sliding the sliding latch 203 with a thumb, the device can be set to a display/data processing mode or a test mode.

By, for example, arranging the sliding latch 203 to a display position of lateral decubitus and then pushing the latch towards the front of the housing, the device is set to the display/data processing mode, thus allowing the user to see the data displayed on a display 204 arranged in the upper case, or besides inputting data to an electrical component within the housing, to perform a command to obtain information related to the test being performed with a manual button 205 arranged adjacent to a data port connector on a rear part of the housing.

Alternatively, by arranging the sliding latch 203 to the test position of lateral decubitus and then pushing the latch towards the front of the housing, the device is set to the test mode. The biosensor is thereby discharged from one of the sensor cavity of the sensor pack 202 and pushed out from a test end 206 of the housing 201, and an electrical contact point on the biosensor is connected to a microprocessor and/or other data processing circuit within the housing. Thus, by applying the sample such as blood to the pushed out biosensor, the user can take out the data relating to the sample, and display the data on the display 204, or can store the data for transmission to other monitoring or analyzing apparatuses via the data port connector.

After the test is finished, the sliding latch 203 is pushed towards the back of the housing and is arranged in an original stand-by position, and the biosensor used in the test is discharged from the housing and the sensor pack 202 is rotated so that the non-used biosensor is moved from the test end 206 to the push-out position.

A biosensor dispensing device disclosed in JP-A 08-285858 (1996) has a sensor bottle 300 shown in FIG. 20A installed therein. In a bottle case 301 of the sensor bottle 300, a plurality of biosensor storing chambers 301a, desiccant storing chambers 301b, and flow paths 301c for communicating the biosensor storing chamber 301a and the desiccant storing chamber 301b are formed. An aluminum seal 302 and an aluminum seal 303 are adhered to both end faces of the bottle case 301, where one biosensor (not shown) is stored in each biosensor storing chamber 301a and one desiccant (not shown) is stored in each desiccant storing chamber 301b, and the desiccant absorbs the moisture entering the biosensor bottle 300, thus preventing a change in performance of the biosensor.

As shown in FIG. 20B, when the biosensor bottle 300 is installed in the biosensor dispensing device including a rotating shaft 305 and a pushing shaft 306, a biosensor bottle driving motor is activated, thus rotating the rotating shaft 305 in one direction and setting the biosensor bottle 300 to an initial position. The rotation of the rotating shaft 305 is performed while checking the position thereof with a photosensor (not shown).

When a measuring button (not shown) is pressed, a pushing shaft driving motor is activated, thus sliding the pushing shaft 306 to the left, which pushing shaft 306 then breaks through the aluminum seal 303 and pushes the biosensor 304. The pushed biosensor 304 breaks through the aluminum seal 302 and moves to a predetermined position and is then measured.

When the measuring button is pushed again after the measurement is finished, the pushing shaft driving motor is activated, thus sliding the pushing shaft 306 slightly towards the left and discharges the biosensor 304 out of the device. The pushing shaft driving motor is thereafter reversed, thus sliding the pushing shaft 306 to the right and returns the shaft to its initial position. The biosensor bottle driving motor is then activated, thus rotating the biosensor bottle 300 to a position at which a next biosensor 304 can be pushed out.

However, in the biosensor dispensing device disclosed in JP-A 8-262026 (1996), since the user must grip and take out the biosensor held at the test end 206 each time the test is finished and, since samples such as blood are applied to the used biosensor, the biosensor is, in the present state, held with for example, a paper and thus is not only complicating, but hygienic problems arise.

Further, since the sensor pack 202 can be loaded to an arbitrary position with respect to the housing 201, an incorrect loading sometimes occurs. That is, when the sensor pack 202 currently being used is taken out for some reasons and a new biosensor is loaded, the sensor pack 202 is sometimes loaded with the sensor holding cavity not containing the biosensor corresponding to the test end 206. In such a case as well, the device starts the operation without recognizing the incorrect loading, and thus the user performs the latch operation a number of times unnecessarily.

Moreover, when setting the device to the display/data processing mode or the test mode, the sliding latch 203 is sled in two-steps, as mentioned above, and thus wrong operation may occur, which is very inconvenient for the user. A cutter (not shown) for discharging the biosensor in the sensor pack 202 is arranged in the housing 201, and thus the user may hurt oneself when loading.

In the biosensor dispensing device disclosed in JP-A 08-285858 (1996), a plurality of sets each including the biosensor storing chamber 301a for storing one biosensor 304, the desiccant storing chamber 301b for storing one desiccant, and the flow path 301c for communicating both chambers, are formed around a center through-hole 301f, and thus the thickness of the biosensor bottle 300 becomes thick even if the number of biosensors 304 stored is few, and the dispensing device including the biosensor bottle 300 can not be made thin.

To appropriately push out and set the biosensor 304 from the biosensor bottle 300 installed in the device, an accuracy of position between the biosensor bottle 300 and the biosensor dispensing device must be set very severely.

When, after removing the biosensor 300 from the device, reloading the biosensor 300 and using such a biosensor, the biosensor bottle 300 is set to the initial position, and thus a setting operation of the biosensor 304 must be sequentially performed from a first biosensor storing chamber 301a, corresponding to the initial position, a second biosensor storing chamber 301a and so on, which in practice, produces a wasteful time until the biosensor 304 is pushed out and set.

Further, since the aluminum sheets 302, 303 are adhered to the end faces of the biosensor bottle 300, there is a danger that the aluminum sheets 302, 303 may be damaged during handling. On the other hand, the biosensor 304 must be able to easily break through the aluminum sheet 302 and be taken out. To this end, a distal end 304a of the biosensor 304 is pointed, and thus when applying the blood, the user may touch the edge thereof and feel pain. The distal end 304 of the biosensor 304 may be a square even if it is hard to break through the aluminum sheet 302, but a point to where the blood should be applied is hard to recognize with a square, and thus is inconvenient.

The present invention aims to provide, in order to solve the above problems, a compact biosensor cartridge and a biosensor dispensing device in which biosensors can be set with a simple operation so that they can be tested one by one, and are protected from moisture until they are set.

DISCLOSURE OF THE INVENTION

The present invention provides, in order to solve the above mentioned problems, a biosensor cartridge for storing a plurality of biosensor in a case and a biosensor dispensing device including the biosensor cartridge, thus sequentially sending out the biosensor with a simple manual operation by a button or a lever and setting the biosensor to a predetermined test position, thus allowing an easy replacement of the biosensor cartridge.

That is, the biosensor cartridge of the present invention is a biosensor cartridge for storing a plurality of biosensors within a case in a stacked manner, and including sensor send-out means for sending out the biosensor in the case one by one and discharging the biosensor from a sensor ejecting port opened at the case. Thus, by driving the sensor send-out means with an external sensor sending out mechanism, the biosensor can be discharged out of the case and the biosensor cartridge can be made smaller and thinner.

The biosensor cartridge of the present invention has the following configurations for examples.

The sensor send-out means includes a cylindrical rotating member rotated by an external sensor sending out mechanism, and a sliding member, engaged so as to be slidable with respect to the rotating member, for sliding with the rotation of the rotating member and pushing a rear end of the biosensor at the bottom layer. Thus, the sliding member directly sends out the biosensor and the load on the biosensor becomes small. Further, a complicating mechanism for discarding the used biosensor becomes unnecessary.

A spiral groove for engaging the sliding member is formed at a cylindrical surface of the rotating member. Thus, as the sliding member slides in the axial direction of the rotating member, the occupying surface area occupied by such members in the case is small, and the biosensor cartridge is made more compact.

The spiral groove is formed over a range of equal to or greater than 360° around a rotating shaft of the rotating member. Thus the play and the shift of the rotating member and the sliding member are absorbed, and the biosensor is reliably moved to a predetermined position.

A sealing member for sealing an opening formed in the case for supporting the rotating member is formed at an end part of the rotating member. Thus, the biosensors within the case are reliably blocked from the outside air which may cause deterioration.

The case is partitioned to a biosensor storing chamber for storing the plurality of biosensors in a stacked manner, and a sliding member housing chamber for housing the sliding member resting at an initial position, at where the rear end of the biosensor in the biosensor storing chamber can be pushed, with a partition wall including an opening having a narrower width than the biosensor. Thus, the biosensor is not pulled in by friction when the sliding member returns to the sliding member storing chamber, and the successive sliding operation of the sliding member is not impeded, and the reliability of sending out the biosensor becomes high.

The opening of the partition wall is set to a width so that a projection formed on the sliding member is able to pass through to push the rear end of the biosensor at the bottom layer. Thus, the sliding member is exited without changing the position and the direction thereof, and a simple mechanism can be used.

A concave part corresponding to an outer shape of valve means for opening/closing the sensor ejecting port is provided on an exterior surface of the case including the sensor ejecting port. Thus, by securely positioning the valve means to the concave part, the sensor ejecting port can be closed.

The sensor send-out means includes a sliding member sled by an external sensor sending out mechanism to push a rear end of the biosensor at the bottom layer. Thus, the sliding member directly sends out the biosensor, and the load on the biosensor becomes small. Further, a complicating mechanism for discarding the used biosensor becomes unnecessary.

A seal plate for opening/closing the sensor ejecting port in synchronization with a sensor discharging operation by the sliding member is provided. Thus, the case is shut out from outside air when the sensor discharging operation is not being performed.

For example, the seal plate is opened by the sliding member.

A spring member for pressing the seal plate towards the sensor ejecting port is provided, where the sliding member is arranged under the biosensor closer to the sensor ejecting port than the front end of the biosensor when the sliding member is at an initial position at where the rear end of the biosensor at the bottom layer can be pushed, guides the biosensor towards the sensor ejecting port during the sensor discharging operation and includes a projection for moving the seal plate against a spring member. Thus, when sending out the biosensor, the front end thereof is protected by the projection. Further, the shape of the biosensor can be freely determined, for example, the front end of the biosensor may be rounded.

The seal plate includes an elastic sealing member pressure welding against an exterior surface of the case around the sensor ejecting port. Thus, sealability enhances when the seal plate closes the sensor ejecting port.

A small projection to which the elastic sealing member is pressure welded at an exterior surface of the case around the sensor ejecting port is provided. Thus, pressure welding against the exterior surface of the case of the elastic sealing member is ensured.

A sealing member for sealing an opening formed in the case for an external sensor sending out mechanism coupled to the sliding member when the sliding member is at the initial position at where the rear end of the biosensor can be pushed is provided. Thus, sealability of the biosensor cartridge when the sensor discharging operation is not being performed is enhanced.

Returning means for returning the sliding member to the initial position at where the rear end of the biosensor can be pushed is provided. Thus, the sliding member can be sled in a direction to discharge the biosensor immediately after discharging the biosensor, or immediately after installing the biosensor cartridge in the biosensor dispensing device, thus eliminating the wasteful time.

The sliding member includes a projection arranged under the biosensor when at the initial position at where the rear end of the biosensor can be pushed. Thus, with the sliding member returned to the initial position after the sensor discharging operation, the sending out of the next biosensor can be reliably performed.

The case is partitioned to a biosensor storing chamber for storing the plurality of biosensors in a stacked manner and a desiccant storing chamber for storing a desiccant with a partition wall, and formed with an air flow path communicating between both storing chambers. Thus, a plurality of biosensors and desiccants are stored in a narrow space, and the biosensor can be prevented from moisture.

A partition wall is provided in the desiccant storing chamber, an air flow path connected to the air flow path communicating to the biosensor storing chamber is formed, and the desiccants are stored along the air flow path. Thus, the drying effect of the desiccant is substantially equally exhibited over a long period of time.

The desiccant is molded as a single body or is divided into a plurality of parts so as to correspond to the shape of the air flow path in the desiccant storing chamber. Thus storing and handling of desiccants are facilitated during assembling of the biosensor cartridge.

A hold-down plate arranged on the biosensor so as to slidably contact the interior surface of the case along a stacked direction of the biosensor, and an elastic body for holding down the biosensor in the stacked direction by way of the hold-down plate are provided. Thus, even if there is an impact and the like from outside the case, the stacked state of the biosensor is satisfactorily maintained and the rear end of the biosensor is pushed with an equal and stable force.

The biosensor has a step-shape in which a thickness is large at a front end and small at a rear end, and the sliding member for pushing the rear end of the biosensor includes a concave part for holding the rear end having a small thickness. Thus, the biosensor can be reliably sent out.

The biosensor has a step-shape in which a thickness is large at a front end and small at a rear end, and the elastic body for holding down the biosensor through the hold-down plate is arranged on a back surface of the hold-down plate at a portion corresponding to the front end region having a large thickness. Thus, a pressure can be equally applied in a well balanced state to the stacked biosensors.

The biosensor dispensing device of the present invention includes a cartridge storing chamber detachably holding a biosensor cartridge for storing a plurality of biosensors in a case in a stacked manner and including sensor send-out means for sending out the biosensor in the case one by one and discharging the biosensor from a sensor ejecting port opened at the case, a sensor sending out mechanism for driving the sensor send-out means in the biosensor cartridge, and a sensor conveying mechanism for conveying the biosensor discharged from the sensor ejecting port by the sensor send-out means to a predetermined test position at where a sample can be applied, inside a body, and an operating part for turning the sensor sending out mechanism ON and OFF outside the body in an exposed manner. Thus, by simply operating the operating part, the biosensor is sequentially arranged at the test position, and a plurality of test can be reliably and continuously performed.

The biosensor dispensing device has the following configurations, for example.

A display unit for acquiring electrical data from the biosensor conveyed to the test position through the electrical circuit within the body, and displaying the data is provided on an exterior surface of the body. Thus, the test result of the biosensor conveyed to the test position can be readily recognized.

Sensor conducting means for pressing and holding the biosensor conveyed to the test position and conducting the biosensor to an electrical circuit within the body is provided. Thus, the biosensor conveyed to the test position is held at such position, and is set to an electrically conductive state.

The cartridge storing chamber can hold the biosensor cartridge including a cylindrical rotating member and a sliding member sliding with the rotation of the rotating member to push the rear end of the biosensor as sensor send-out means, the sensor sending out mechanism includes rotating means for rotating the rotating member of the biosensor cartridge, and the operating part is configured so as to move the sensor sending out mechanism with a forefinger while gripping the body with one hand. Thus, by simply operating the operating part while holding the body with one hand, the biosensor can be arranged at the test position, and a plurality of tests can be reliably and continuously performed.

The operating part freely exits from the body, and when pushed into the body, operates the sensor sending out mechanism. Thus, the operation of the operating part to arrange the biosensor at the test position can be reliably performed.

The sensor sending out mechanism drives the sensor send-out means to discharge the biosensor in a direction opposite the direction of pushing in the operating part. Thus, the width of the device can be set small.

Valve means for opening/closing the sensor ejecting port opened at the case of the biosensor cartridge is provided. Thus, the sensor ejecting port is opened only when necessary, thereby preventing deterioration of the non-used biosensors in the case.

The valve means is a roller rolling over the exterior surface of the case including the sensor ejecting port. Thus, the sensor ejecting port is reliably opened/closed without impeding the operations of for example, the sensor send-out means.

The sensor conducting means and the valve means are gear-coupled to the sensor sending out mechanism. Thus, by operating the operating part without the user paying particular attention, a series of operations of discharging the biosensor in the biosensor cartridge from the sensor ejecting port and arranging the biosensor at the test position while opening/closing the sensor ejecting port as appropriate, holding the biosensor arranged at the test position at such position, and setting to an electrically conductive state can be easily and reliably performed. Therefore, mistaken discharge of the biosensor or careless exposition of the inside of the biosensor cartridge to the atmosphere can be prevented.

For example, each link member supporting the sensor conducting means and the valve means each on one end is axially supported on the body, and a cam for holding and turning the other end of each link member is provided on the operating part.

With one operation of the operating part, the biosensor is conveyed to the test position, is conducted to the electrical circuit within the body, and set to a test state. Thus, an unnecessary operation is eliminated and the biosensor can be reliably set.

A power source of the body is driven when the biosensor is set to the test state. Thus, at the start of the test of applying a sample to the biosensor, an electrical signal can be acquired from the biosensor, and thus the test can be smoothly performed.

The biosensor at the test position is discharged out of the body with the operation of the operating part after the biosensor is set to the test state. Thus, when setting a new biosensor to a test state by the operating part or to a stand-by state for setting, the used biosensor is automatically discharged, and a plurality of tests can be smoothly performed.

A cartridge holding mechanism for unremovably holding the biosensor cartridge is provided. Thus, careless removal of the cartridge during the operation is prevented.

The cartridge holding mechanism is gear-coupled to the operating part. Thus, the cartridge holding mechanism can be reliably operated without using a special electrical engine.

Detection means for detecting the return of the operating part to the initial position is provided. Thus, the position of the operating part is reliably detected, thus preventing the breakdown of the device.

The detection means recognizes a contact with a member configuring one part of the operating part. Thus, the position of the operating part can be detected using the members equipped in the operating part.

The sensor sending out mechanism includes connection switching means for connecting or releasing connection with respect to the sensor send-out means of the biosensor cartridge in cooperation with the opening/closing operation of a lid body that opens/closes the cartridge storing chamber when attaching and detaching the biosensor cartridge. Thus, with the opening of the lid body prior to removing the biosensor cartridge, connection is automatically released, and does not become a hindrance to the removing operation and the handling thereof is improved. After installing the biosensor cartridge, connection is automatically made with the closing of the lid body, and the biosensor in the cartridge can be efficiently discharged.

A nail member is provided on the operating part in an oscillating manner, a sliding path on which a distal end of the nail member slides is formed in an inner wall of the body, and a saw-blade concavo-convex part for locking the distal end of the nail member and position fixing the operating part when the operation of the operating part is stopped is arranged on the sliding path. Thus, even if the operation of the operating part is interrupted, the setting operating can be continued without the operating part returning to the initial position. Therefore, trapping of the biosensor is avoided.

The sliding path is configured in a loop-form by arranging, in series, an outward path on which the distal end of the nail member slides when the operating part is pushed in and a homeward path on which the distal end of the nail member slides when the operating part returns to the initial position, and the saw-blade concavo-convex part is arranged on the outward path. Thus, the movement of the operating part can be reliably controlled, and a mechanism for holding the operating part at a series of positions can be made small.

A latch mechanism for locking the operating part at a position at where the biosensor is set to the test state with respect to the body is provided. Thus, by holding the position of the operating part, the biosensor can be held at the set state, and the test operation can be easily and stably performed.

For the latch mechanism, a latch projection is provided on the operating part and a latch body part for locking the latch projection is provided in the body. Thus, the latch mechanism can be obtained with a simple member.

The cartridge storing chamber can hold the biosensor cartridge including a sliding member for pushing the rear end of the biosensor as the sensor send-out means, the sensor sending out mechanism includes a pushing member for pushing and sliding the sliding member of the biosensor cartridge, and the operating part is configured so as to electrically operate the sensor sending out mechanism. Thus, by simply operating the operating part, the biosensor can be arranged at the test position, and the test can be reliably and continuously performed over a number of times.

The seal plate for opening/closing the sensor ejecting port of the biosensor cartridge is configured to open only when discharging the biosensor. Thus, the flow-in time of the outside air into the biosensor cartridge becomes extremely short.

The pushing member of the sensor sending out mechanism is provided so as to freely exit towards the sliding member of the biosensor cartridge and detection means for detecting an operation stroke of the pushing member is provided. Thus, while detecting operation stroke of the pushing member with the detection means, the pushing member can be accurately arranged between the push-in position at where the biosensor is arranged at a predetermined test position and the initial position.

Detection means for detecting a position of the biosensor conveyed to a predetermined test position by the sensor conveying mechanism is provided. Thus, the biosensor can be accurately arranged at the test position.

The sensor sending out mechanism and the sensor conveying mechanism are independently operable. Thus, a highly reliable dispensing device is configured with a simple configuration, and the operating time can be shortened.

BRIEF DESCRIPTION OF THE DRAWINGS

FIG. 14A is a side cross sectional view of a biosensor cartridge loaded in the biosensor dispensing device of FIG. 13;

FIG. 14B is an end cross sectional view of a biosensor cartridge loaded in the biosensor dispensing device of FIG. 13;

FIG. 19A is an external perspective view of a conventional biosensor dispensing device;

FIG. 19B is an interior view of the conventional biosensor dispensing device;

BEST MODE FOR CARRYING OUT THE INVENTION

Hereinafter, embodiments of the present invention will be described with reference to the drawings.

First Embodiment

A biosensor dispensing device according to a first embodiment of the present invention will now be described with reference to FIGS. 1 to 12. This biosensor dispensing device is used in, for example, blood-glucose measurement.

Figure 1:
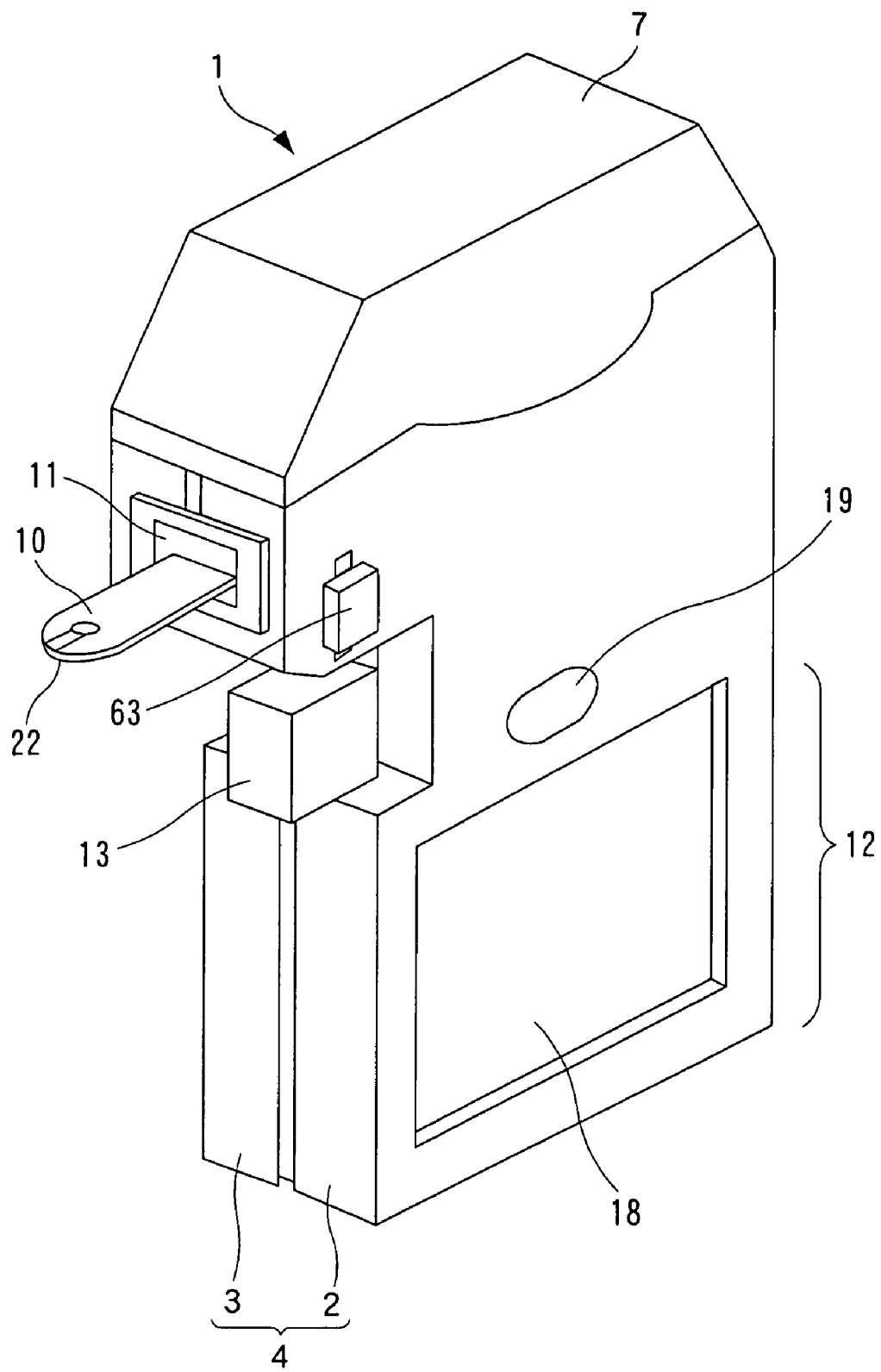
FIG. 1 is a perspective view of a biosensor dispensing device according to a first embodiment of the present invention.
Figure 2:
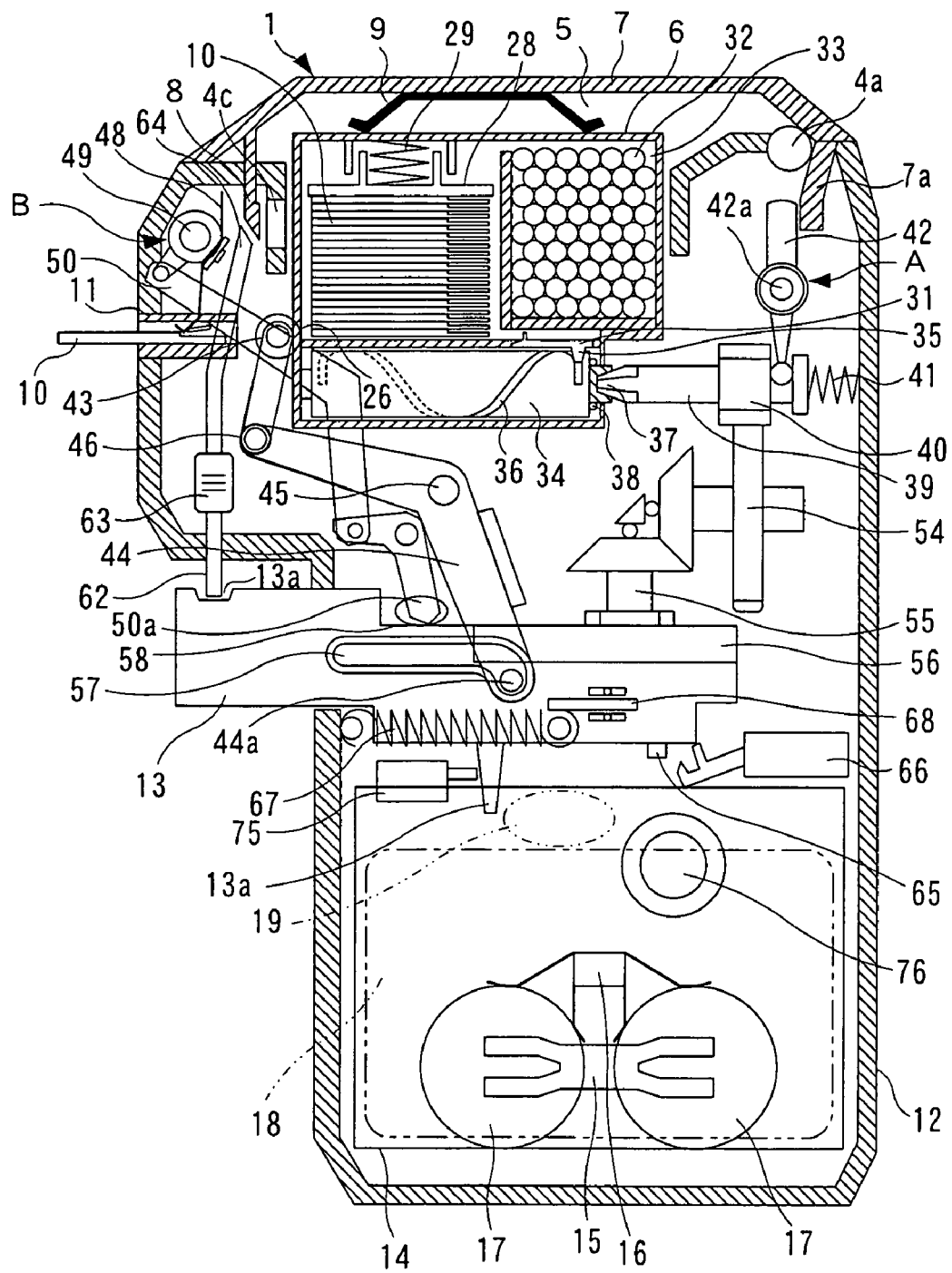
FIG. 2 is a cross sectional view of the biosensor dispensing device of FIG. 1.

In FIGS. 1 and 2, the biosensor dispensing device 1 includes a substantially rectangular body 4 configured with a body upper case 2 and a body lower case 3 arranged facing each other, and a biosensor cartridge 6 can be stored in a cartridge storing chamber 5 in the vicinity of an opening opened on one side of the body 4. A biosensor sending out mechanism A for sending out the biosensor from the biosensor cartridge 6 and a biosensor conveying mechanism B for conveying the biosensor discharged from the biosensor cartridge 6 to a predetermined test position are arranged on both sides of the cartridge storing chamber 5.

The opening of the body 4 is opened and closed with a cartridge loading cover 7 rotatably attached about a shaft center of a shaft 4a. A cover hook 8 for locking the cartridge loading cover 7 to the body 4, and a pressing spring 9 for pressing the biosensor cartridge 6 towards a rib (not shown) of an interior surface of the body supporting a bottom of the biosensor cartridge 6 are provided on the interior surface of the cartridge loading cover 7. The following explanation is given with the shown direction as the vertical direction.

A sensor guide 11 for guiding the biosensor 10 discharged from the biosensor cartridge 6 to the test position is provided on the upper side (substantially the half closer to the opening) and the side part (e.g., left side in the direction with the body upper case 2 arranged in the near side) of the body 4.

The lower part (substantially the half distant from the opening) of the body 4 has a dimension set so as to serve as a grip 12 for the user, and has a somewhat narrower width than the upper part of the body 4. One end of a columnar operating actuator 13 for sending out the biosensor 10 is projected from the upper part and the side part (left side, similar to the sensor guide 11) of the grip 12.

A printed wiring board 14 formed with a signal processing circuit and a control circuit, battery electrodes 15, 16, and a battery 17 are arranged inside the grip 12, and a display screen 18 of a liquid crystal display unit and an operating button 19 for displaying the information to be displayed on the display screen 18 or inputting information to the circuit on the printed wiring board in accordance with the display of the display screen 18 are arranged on an exterior surface of the grip 12. A microprocessor (not shown) and the like for processing, storing and/or displaying on the display screen 18 the data generated during the test operation is also provided in the circuit on the printed wiring board 14.

Figure 3:
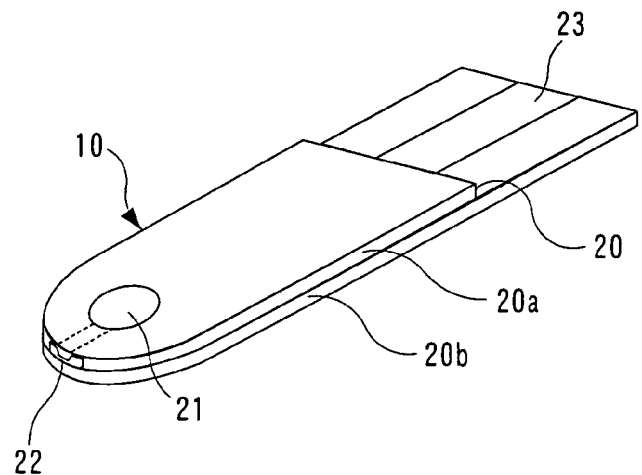
FIG. 3 is a perspective view of a biosensor dispensed from the biosensor dispensing device of FIG. 1.

As shown in FIG. 3, the biosensor 10 is configured by stacking a short upper layer sheet 20a with one rounded end and a long under layer sheet 20b made of polyethylene terephthalate (PET) and the like, thus including a step 20, a reagent part 21 (or a biological sensing part) containing enzyme is arranged in the vicinity of the above-mentioned one end, where the above-mentioned one end communicating to the reagent part 21 by means of a capillary tube serves as an applying part 22, and an electrode 23 extending to the reagent part 21 is provided on an exposed surface of the under layer sheet 20b.

Figure 4:
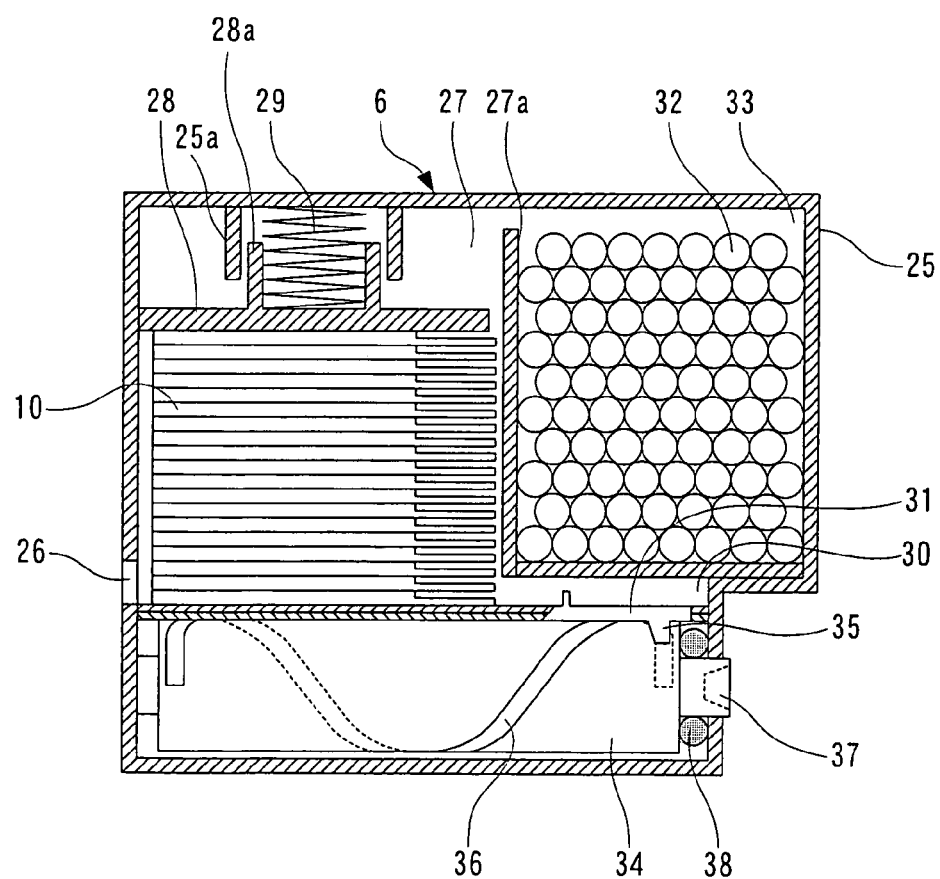
FIG. 4 is a cross sectional view of a biosensor cartridge loaded in the biosensor dispensing device of FIG. 1.

As shown in FIG. 4, with regards to the biosensor cartridge 6, a biosensor ejecting port 26 is formed at the lower part of the cartridge case 25, and a biosensor storing chamber 27 facing the biosensor ejecting port 26 is partitioned by a partition wall 27a in the vertical direction. The cartridge case 25 is configured by arranging a cartridge upper case and a cartridge lower case so as to face each other, and is made of a material which practically does not have water permeability, for example, PP, with a wall thickness of equal to or greater than 1 mm, thus ensuring water-proof property of the biosensor cartridge 6.

A plurality of biosensors 10 are stacked inside the biosensor storing chamber 27, a hold-down plate 28 is arranged on the stacked biosensor 10, and a sensor pressing spring 29 is arranged between the hold-down plate 28 and a roof surface of the cartridge case 25. Ribs 28a, 25a are formed at the roof surface of the hold-down plate 28 and the cartridge case 25 so as to surround the sensor pressing spring 29 and so as to slidably contact each other, and the hold-down plate 28 is pressed by the sensor pressing spring 29 and is guided by the ribs 28a, 25a, thus holding down the biosensor 10 in the stacked direction. The position of the sensor pressing spring 29 is a position corresponding to an upper layer sheet of the biosensor 10.

A pushing member 31 for pushing the biosensor 10 at the bottom layer towards the biosensor ejecting port 26 is housed inside a pushing member housing chamber 30 communicating with the biosensor storing chamber 27 at an opening at a lower end of the partition wall 27a.

The biosensor storing chamber 27 has a sealed configuration, to be hereinafter described, and is communicated to a desiccant chamber 33 filled with desiccants 32 at an opening at an upper end of the partition wall 27a, thus maintaining each biosensor 10 in a dry state.

A cylindrical pushing rotating member 34 for operating the pushing member 31 is housed at the bottom part of the cartridge case 25. The pushing rotating member 34 is supported in a freely rotating manner to the cartridge case 25 at a supporting part formed in a projecting manner on both ends, and includes a spiral groove 36 with which an engaging projection 35 formed at a lower surface of the pushing member 31 slidably engages.

The supporting part of one end of the pushing rotating member 34 passes through the cartridge case 25 and includes a concave drive-coupling part 37 for transferring rotation-drive from the outside to the pushing rotating member 34, and outer packages a ring-shaped packing 38 for sealing the pass-through portion of the cartridge case 25.

Figure 5:
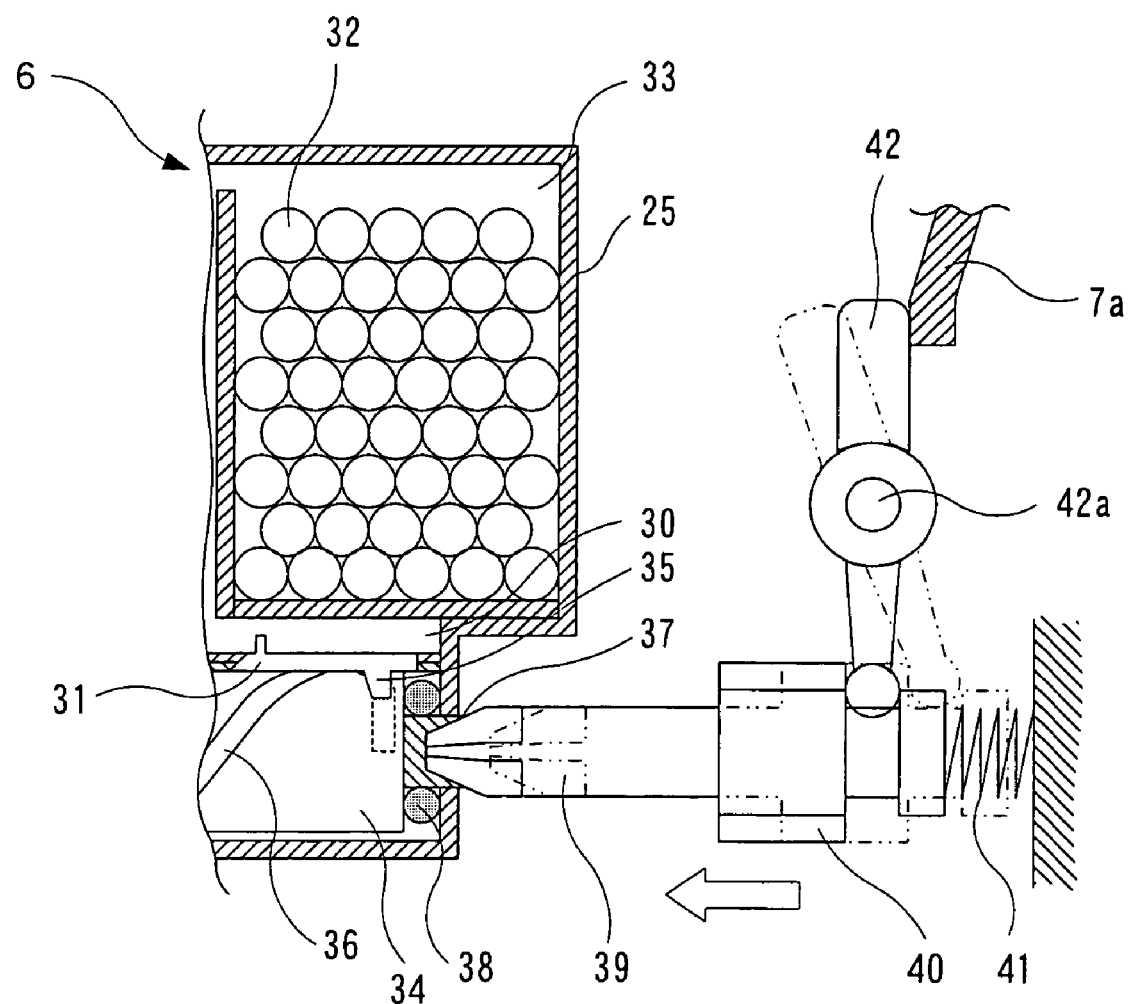
FIG. 5 is a partial sectional view illustrating an operation of a sensor sending out mechanism for sending out the biosensor from the biosensor cartridge of FIG. 4.

As shown in FIG. 5, a third driving gear 40 having a drive-transferring pin 39 that fits into the drive-coupling part 37 of the pushing rotating member 34 on one end, a gear thrust spring 41 for biasing the third driving gear 40 towards the biosensor cartridge 6, and a gear slide lever 42 for moving the third driving gear 40 away from the biosensor cartridge 6 against the gear thrust spring 41 are arranged in the vicinity of the cartridge case 25. The gear slide lever 42 is freely rotatable about a shaft 42a with an operating projection 7a projected from the cartridge loading cover 7.

In a state in which the cartridge loaded cover 7 is closed, the third driving gear 40 approaches the biosensor cartridge 6 with a bias force of the gear thrust spring 41 and the drive transferring pin 39 is coupled to the drive-coupling part 37. When the third driving gear 40 is rotated in this state, the pushing rotating member 34 coupled to the third driving gear 40 through the drive transferring pin 39 and the drive-coupling part 37 is rotated, and the pushing member 31 engaged with the spiral groove 36 of the pushing rotating member 34 with the engaging projection 35 is exited. When opening the cartridge loaded cover 7, the operating projection 7a rotates the gear slide lever 42 in a counterclockwise direction, which gear slide lever 42 moves the third driving gear 40 in a direction away from the biosensor cartridge 6, thus releasing the coupling of the drive transferring pin 39 and the drive-coupling part 37.

Figure 6:
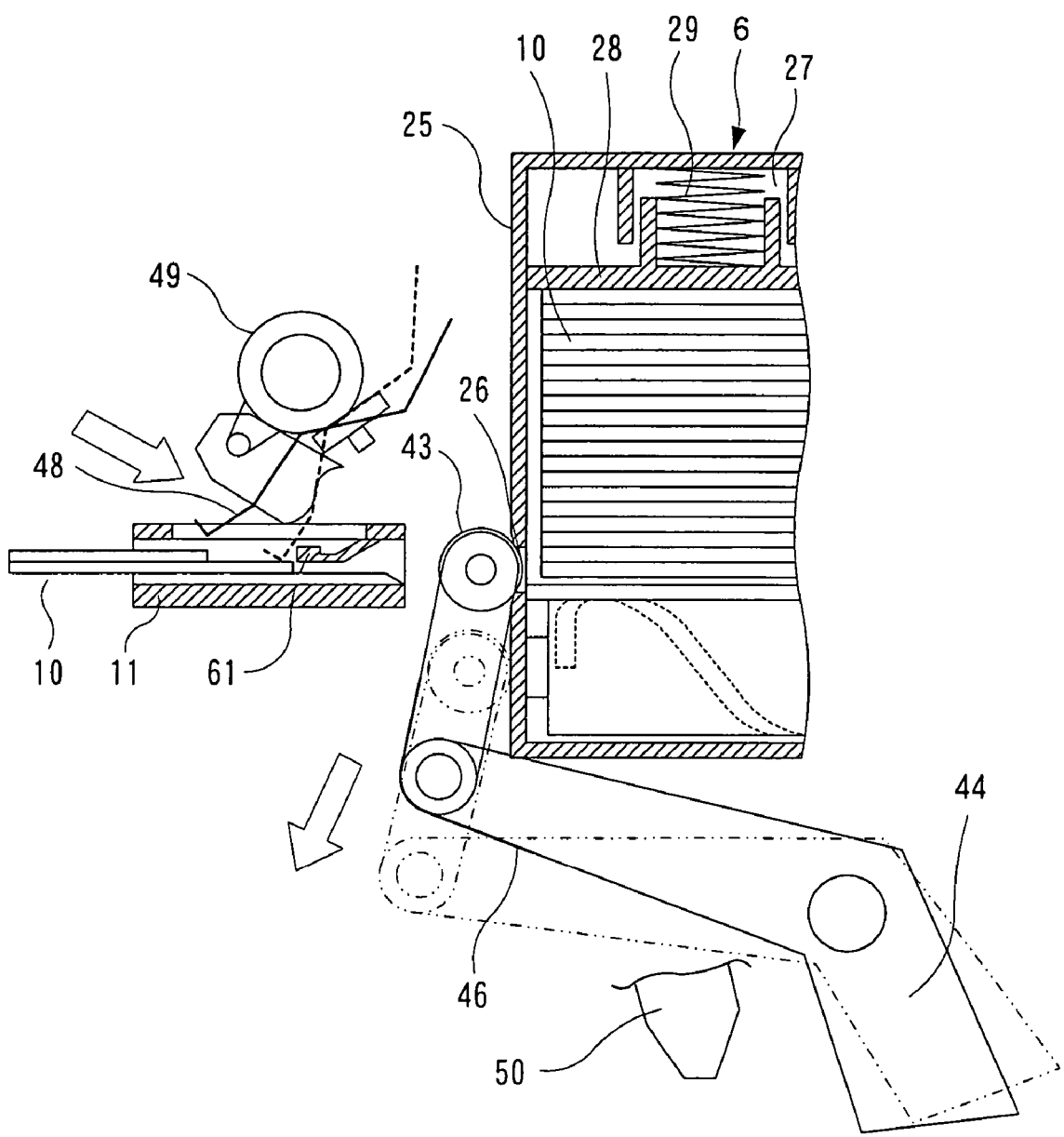
FIG. 6 is a partial sectional view illustrating an operation of a sealing mechanism for sealing the biosensor cartridge of FIG. 4.
Figure 7:
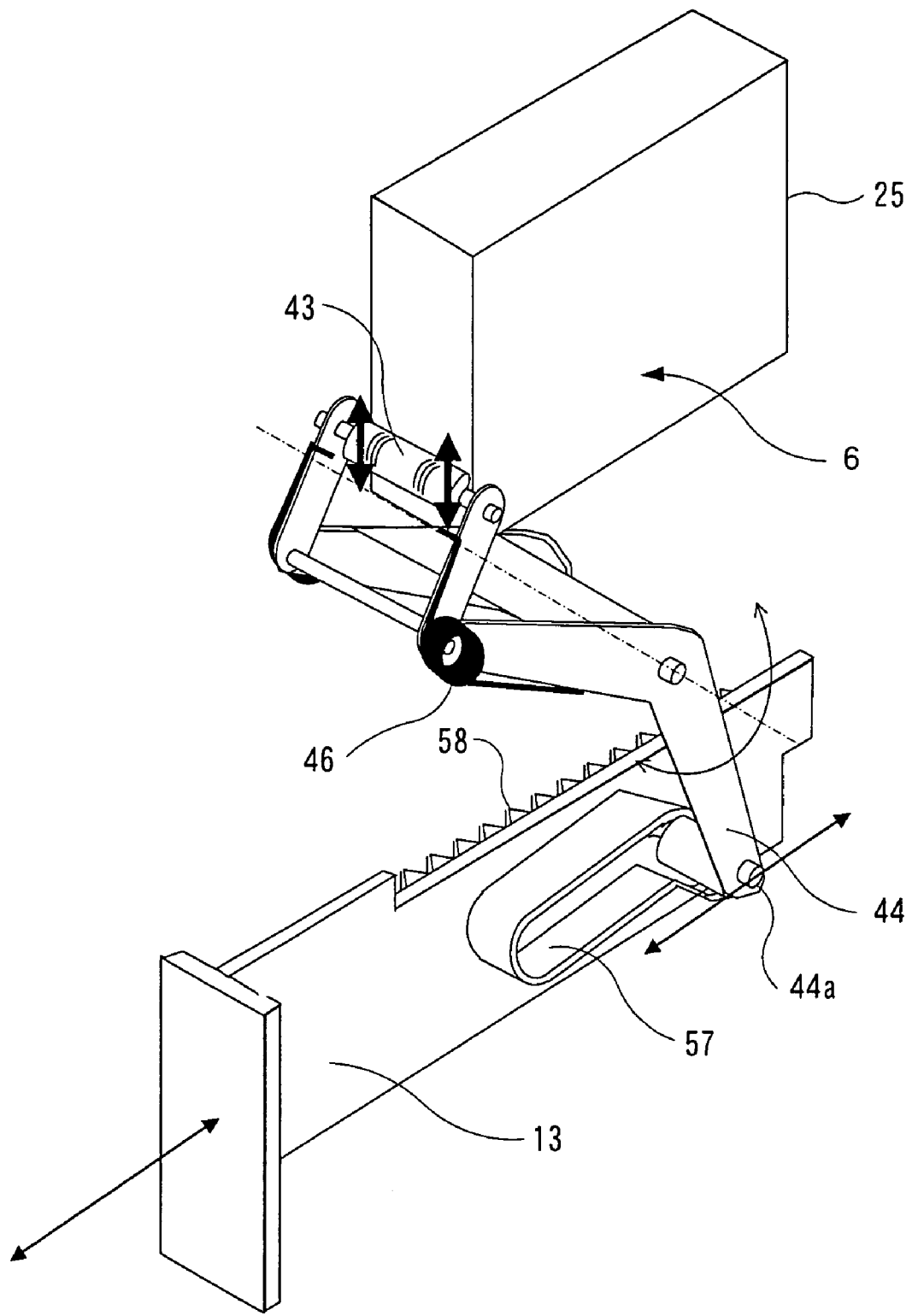
FIG. 7 is a perspective view of the sealing mechanism of FIG. 6.

As shown in FIGS. 6 and 7, a sealing roller 43 for sealing the biosensor ejecting port 26 is arranged in the vicinity of the biosensor cartridge 6.

A sealing roller supporting link 44 supporting the sealing roller 43 on one end is made of two members, is attached to the operating actuator 13 at the other end, and a sealing roller pressurizing spring 46 for applying, to the sealing roller 43, a pressure welding force acting towards the biosensor ejecting port 26 is arranged at the coupling part.

The sealing roller pressurizing spring 46 is set to a load that does not inhibit operability when, for example, installing the biosensor cartridge 6 to the body 4, or set to, for example, a load equal to or less than 1 to 2 N (about 100 to 200 gf). With regards to the sealing roller 43, an elastic body or an elastomer such as silicon rubber, NBR (nitrile rubber) or EPDM (ethylene propylene copolymer), a material having a low compressive residual strain is used for the surface, and thus adaptation and adhesiveness to the biosensor cartridge 6 made of for example, PP, as mentioned above is ensured.

A surface region of the cartridge case 25 including the biosensor ejecting port 26 is formed in a concave shape along the line of an outer shape of the sealing roller 43 so as to increase a contacting surface of the sealing roller 43.

As shown with a solid line, when the sealing roller supporting link 44 is in an extended state, the sealing roller 43 is pressure welded to the biosensor ejecting port 26 with the help of the operation of the sealing roller pressurizing spring 46, thus sealing the biosensor ejecting port 26. When the other end of the sealing roller supporting link 44 is moved from this state, as shown with a broken line, the sealing roller supporting link 44 is bent, thereby moving the sealing roller 43 away from the biosensor ejecting port 26, and the biosensor 10 can then be sent out. During the sending-out of the biosensor 10 of when the sealing roller 43 is moved away from the biosensor ejecting port 26, the biosensor storing chamber 38 is exposed to the atmosphere, but the non-used biosensor 10 therein is exposed to the atmosphere only for a short time and thus there is no great influence on the dry state.

Figure 8:
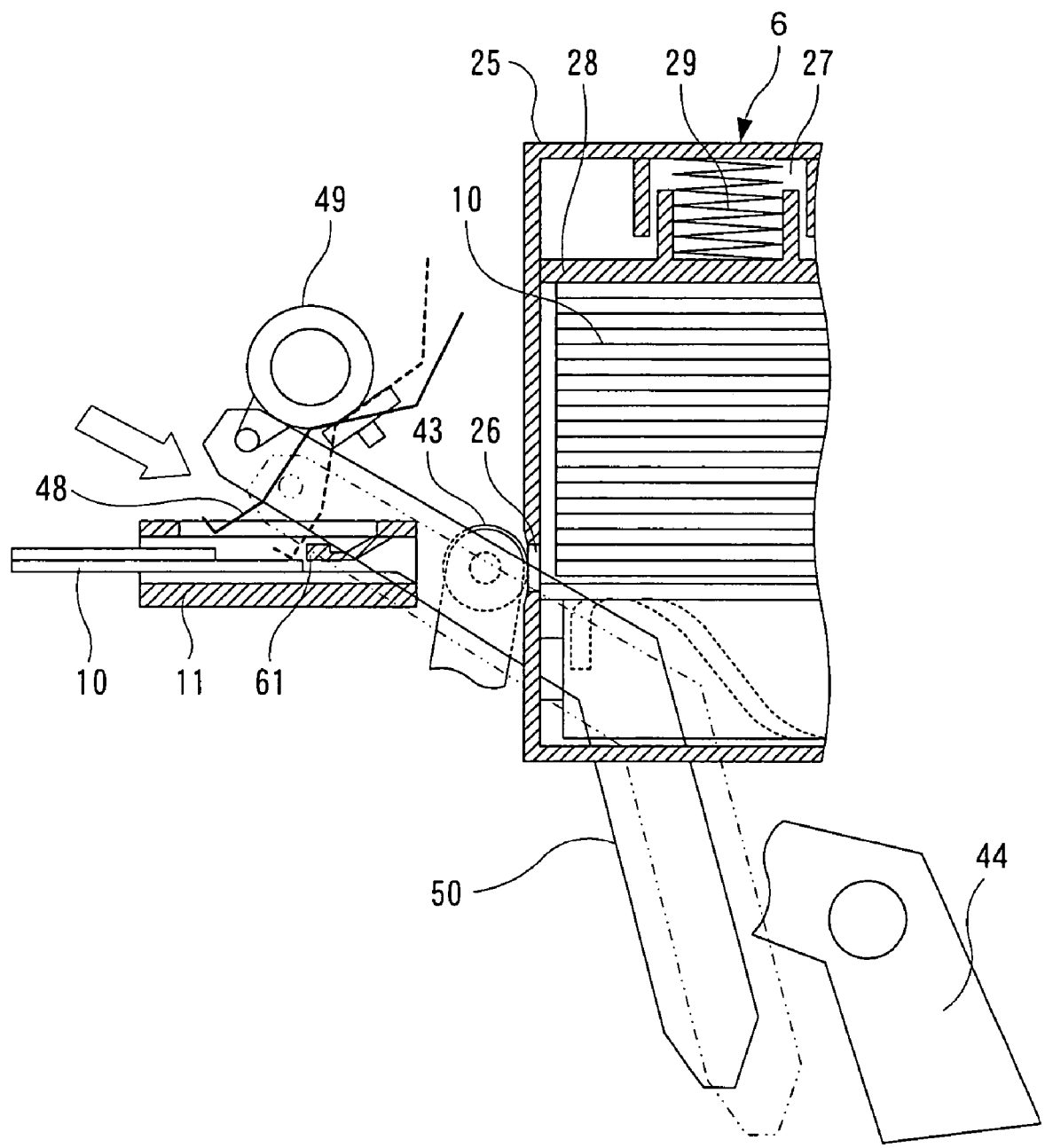
FIG. 8 is a partial sectional view illustrating an operation of an electrically conducting mechanism for electrically conducting the biosensor discharged from the biosensor cartridge of FIG. 4.
Figure 9:
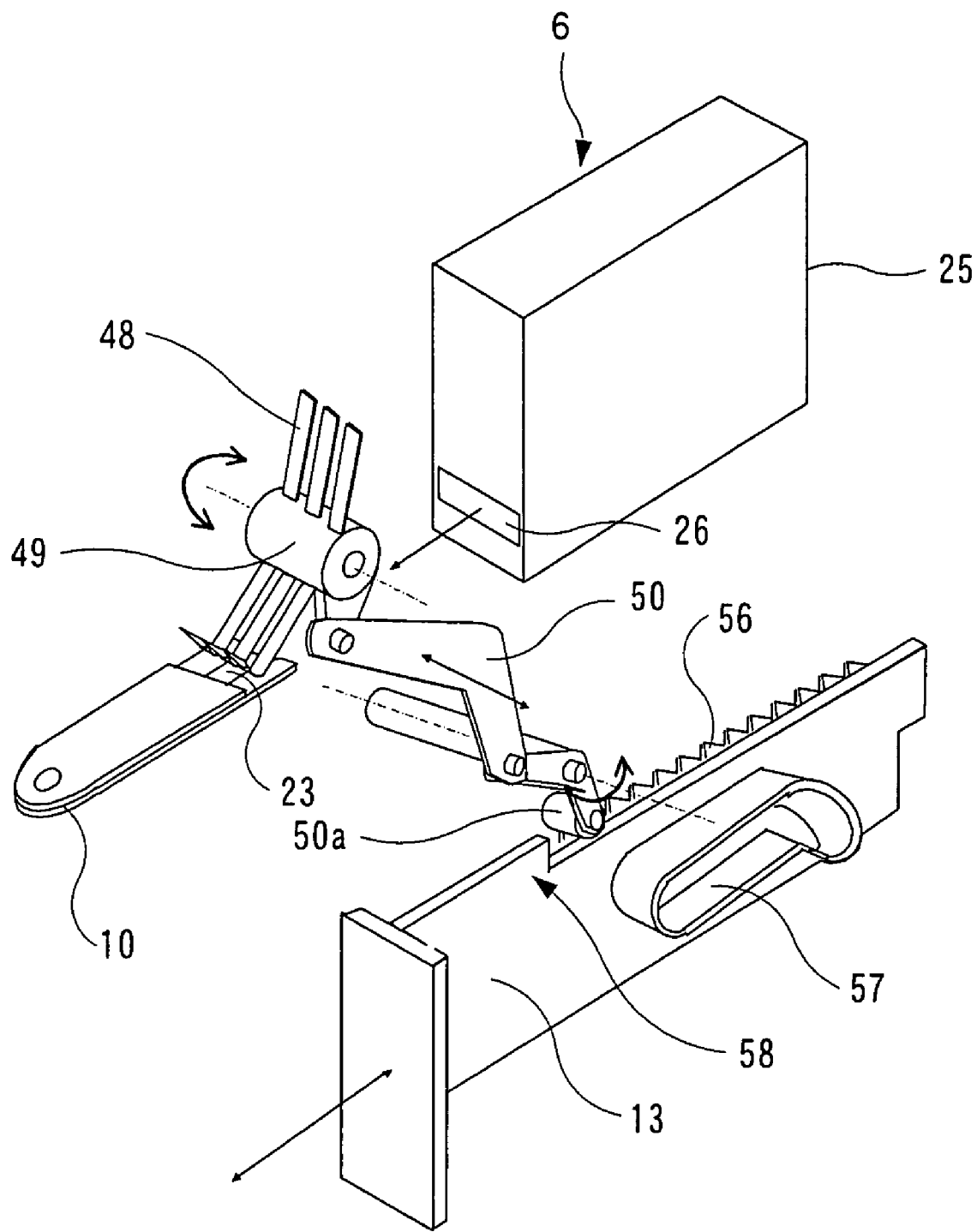
FIG. 9 is a perspective view of the electrically conducting mechanism of FIG. 8.

As shown in FIGS. 8 and 9, an electrode arm 48, attached to an electrode arm rotation operating part 49, for supplying voltage to the electrode part 23 of the biosensor 10 discharged to the sensor guide 11 is arranged in the vicinity of the sensor guide 11. The electrode arm rotation operating part 49 is attached to one end of an electrode arm rotation link 50, and the electrode arm rotation operating part 49 is rotated with the movement of the other end of the electrode arm rotation link 50, thus arranging the electrode arm 48 between a position distant from the biosensor 10, as shown with a solid line, and a position pressure welded to the electrode part 23 of the biosensor 10, as shown with a broken line.

Figure 10A:
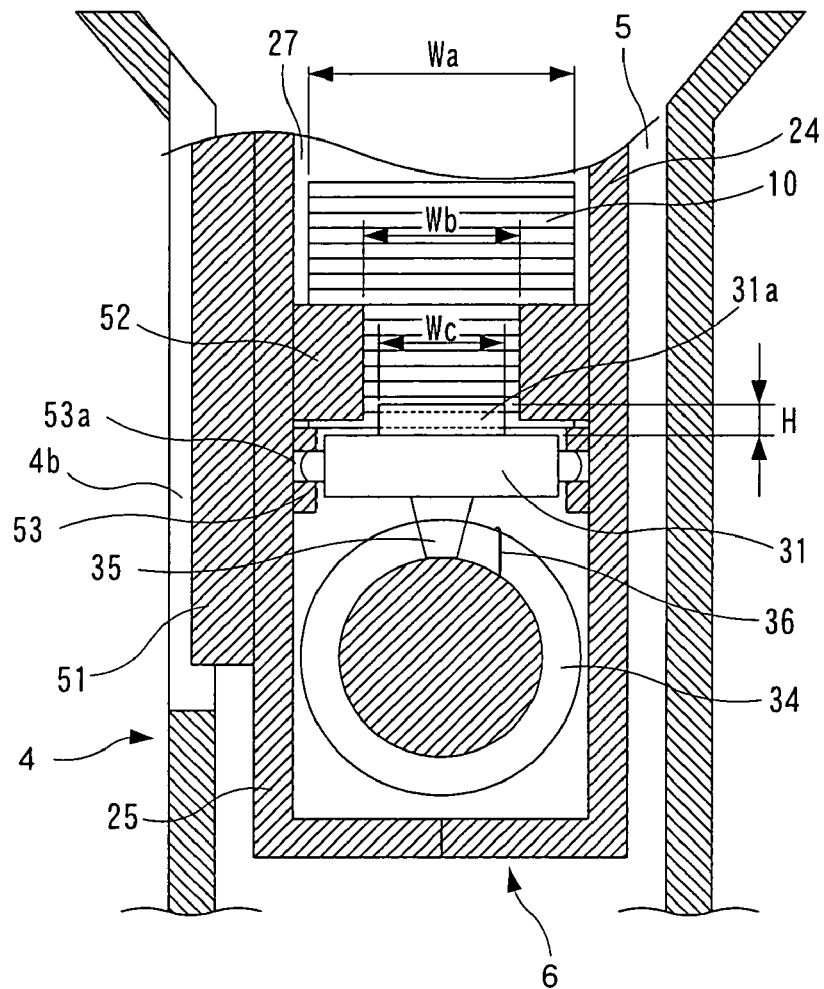
FIG. 10A is a longitudinal sectional view of the biosensor cartridge of FIG. 4.

As shown in FIG. 10A, a wrong-installation preventing member 51, engaging with a concavo-convex part 4b provided at an inner wall of the body 4, is arranged on an exterior surface of the cartridge case 25 to prevent wrong installation to the cartridge storing chamber 5. A sensor return rib 52 contacting the end faces of the stacked biosensors 10 and a sensor receiving rib 53, including a pushing member guiding groove 53a for guiding the movement of the pushing member 31 at the center, for receiving the bottom layer biosensor 10 are formed at the interior surface of the cartridge case 25.

A gap Wb between the sensor return ribs 52 is set so as to be greater than the width Wc of the projection 31a of the pushing member 31 and smaller than the width Wa of the biosensor 10, and thus does not inhibit the sliding operation of the pushing member 31 of when pushing the biosensor 10. Further, after the pushing operation is finished, the biosensor 10 does not enter the pushing member storing chamber 30 during the returning operation in which the pushing member 31 returns to the initial position or when carrying the biosensor dispensing device 1. The height H of the projection 31a of the pushing member 31 is set smaller than the thickness of one biosensor 10 so that one stacked biosensor 10 at the bottom layer is reliably pushed out.

Figure 10B:
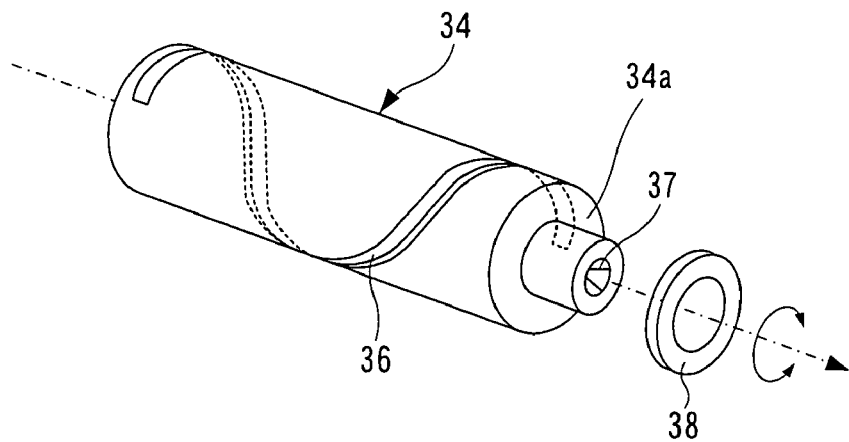
FIG. 10B is a perspective view of a pushing rotating member provided at a lower part of the biosensor cartridge of FIG. 4.

As shown in FIG. 10B, the spiral groove 36 of the cylindrical surface of the pushing rotating member 34 with which the engaging projection 35 of the pushing member 31 engages is formed in a range of equal to or greater than 360 degrees around the shaft center in a direction encircling the shaft center, and both end portions of the spiral groove 36 are formed to a predetermined length in a direction orthogonal to the shaft center (circumferential direction), and thus absorbs plays and shifts of the pushing rotating member 34 or the pushing member 31, and moves the pushing member 31 by a distance that reliably arranges the biosensor 10 at the predetermined position.

Referring again to FIG. 2, the third driving gear 40 for rotating the pushing rotating member 34 is coupled to a rack 56 integrally formed on the operating actuator 13 through a second driving gear 54 and a first driving gear 55, and the direction of pushing the biosensor 10 is reversed 180 degrees with respect to the sliding direction of the operating actuator 13. The dimension of the width of the device is thereby suppressed.

The pushing member 31, the biosensor 10 at the bottom layer, and the electrode arm 48 are positionally set so as to be substantially collinear, and the operations of pushing to setting to the test position of the biosensor 10 are performed continuously with the movement of the operating actuator 13.

The electrode arm rotation link 50 for rotating the electrode arm 48 is driven by starting a contact with the electrode rotation link follower 50a by an electrode arm rotation link cam 58 from a predetermined position.

The sealing roller supporting link 44 with the sealing roller 43 attached to one end thereof is held by a sealing roller supporting cam 57 of the operating actuator 13 with a sealing roller supporting link follower 44a attached to the other end thereof.

Figure 11:
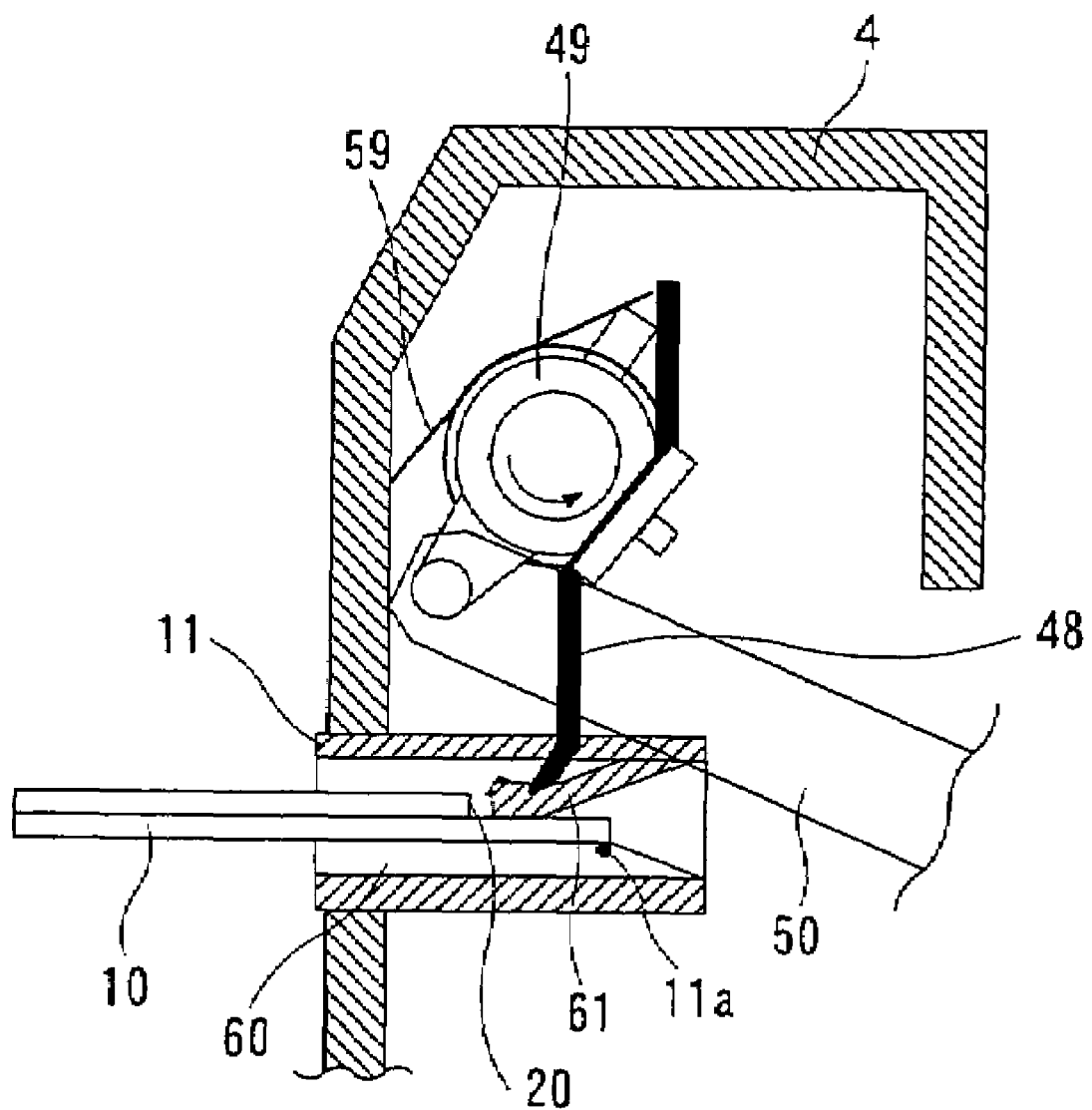
FIG. 11 is a cross sectional view showing a set state of the biosensor in the biosensor dispensing device of FIG. 1.

As shown in FIG. 11, an electrode arm rotation spring 59 for rotating the electrode arm rotation operating part 49 in a direction to push the electrode arm 48 downwards is attached to the electrode arm rotation operating part 49 attached with the electrode 48. With regards to the sensor guide 11, a biosensor receiving rib 60 is provided at the bottom, and a sensor return stopper 61 made of an elastic material such as a resin spring for stopping the return of the biosensor 10 is provided at the roof in a diagonally downward direction.

Therefore, the biosensor 10 discharged to the sensor guide 11 slides in the shaft direction until the step 20 passes through the sensor return stopper 61, and the electrode part 23 is pushed by the electrode arm 48. The electrode arm 48 rotates about the shaft of the electrode arm rotation operating part 49 while pushing the electrode part 23, and thus draws back the biosensor 10. However, since the biosensor return stopper 61 contacts the step 20 of the biosensor 10 and stops the return of the biosensor, the biosensor 10 is reliably set to the test position at where the front end thereof projects out of the body 4 by a predetermined amount.

Referring again to FIG. 2, an operating actuator fixing pin 62 capable of engaging with a concave part 13a formed on the upper surface of one end of the operating actuator 13 is coupled to a lock button 63 arranged on the exterior surface of the body 4, and by sliding the lock button 63 downwards, the operating actuator fixing pin 60 is engaged with the concave part 13a, thereby locking the operating actuator 13.

A lock coupling rod 64 capable of pressing the cover hook 8 of the cartridge loaded cover 7 is integrally formed at the lock button 63, and by sliding the lock button 63 upwards, the lock coupling rod 64 is raised thus pressing and engaging the cover hook 8 to a hole 4c formed in the body 4, thereby locking the cartridge loaded cover 7 so as not to turn with respect to the body 4.

A sequence of operations of the biosensor dispensing device 1 will now be described.

The biosensor cartridge 6 is loaded in the body 4, the cartridge loaded cover 7 is closed, and the lock button 63 is sled upwards. The operating actuator fixing pin 62 is thereby raised and the operating actuator 13 is lock released, and the lock coupling rod 64 is raised thus pushing the distal end of the cover hook 8 of the cartridge loaded cover 7, and locking the cartridge loaded cover 7 with respect to the body 4.

Subsequently, the operating actuator 13 is pushed into the body 4. The sealing roller supporting link follower 44a is thereby sled on the sealing roller supporting link cam 57 of the operating actuator 13, and the sealing roller 43 at one end of the sealing roller supporting link 44 is rolled and moved over the surface of the biosensor cartridge 6, thus releasing the sealing of the biosensor ejecting port 26.

Further, the first driving gear 55 engaged with the rack 56 of the operating actuator 13 is rotated, which rotation is transferred to the second driving gear 54, then to the third driving gear 40, thus rotating the pushing rotating member 34 coupled to the drive transferring pin 39 of the third driving gear 40 with the drive-coupling part 37, and sliding the pushing member 31 engaged with the pushing rotating member 34.

The biosensor 10 at the bottom layer is then pushed, ejected from the biosensor ejecting port 26 and discharged to the sensor guide 11, and the applying part 22 of the front end is arranged at the test position exteriorly exposed. Here, when the biosensor 10 contacts a detection switch 11a provided in the sensor guide 11, the power source of the biosensor dispensing device 1 is turned ON and the biosensor dispensing device 1 is set to the test mode.

The electrode arm rotation link 50 coupled to the electrode arm rotation link cam 58 of the operating actuator 13 by way of the electrode arm rotation link follower 50a is pulled, causing the electrode arm rotation operating part 49 at one end thereof to rotate, thereby rotating the electrode arm 48 and electrically contacting the electrode part 23 of the biosensor 10 and pressing and holding the biosensor 10.

When a fluid (e.g., blood accumulated at the finger after puncturing the finger of a human being) is applied to the applying part 22 of the biosensor 10, a portion of the fluid is drawn into the capillary tube extending from the applying part 22 to the reagent part 21, and the fluid of an amount sufficient for testing is drawn into the reagent part 21. As a result of a chemical reaction of the blood-glucose or a measurement object component in the fluid and a reagent, an electrical signal corresponding to the blood-glucose level is sent to the printed wiring board 14 through the electrode part 23 and the electrode arm 48, and is for example, processed and stored in the circuit.

Since the biosensor dispensing device 1 is activated to the display mode when the biosensor 10 is arranged at the test position, the information related to the biosensor cartridge 6 and the performed test is displayed on the display screen 18 with the operation button 19. The information can also be input to the circuit of the printed wiring board 14 in accordance with the display of the display screen 18.

Here, the operating actuator 13 is attached so that one end thereof projects from the side of the body 4, and thus when gripping the grip 12 and operating the operating actuator 13 (especially with a right hand), the visibility of the display screen 18 is not blocked.

After the test is finished, and acquiring of information or inputting of data is completed, the operating actuator 13 is further pushed into the body 4, thus causing the electrode arm rotation link 50 coupled to the electrode arm rotation link cam 58 of the operating actuator 13 by way of the electrode arm rotation link follower 50*a* to be pulled and the electrode arm rotation operating part 49 of one end thereof to be rotated, which causes the electrode arm 48 to be rotated and the returning operation thereof allows the biosensor 10 to be discharged out of the body 4. The pushing member 31 is then returned to the initial position, and the biosensor dispensing device 1 is set to the OFF or the stand-by state.

The operating actuator 13 will now be described in detail.

As described above, by operating the operating actuator 13, a series of operation is output from the rack 56, the electrode arm rotation link cam 58 and the sealing roller supporting link cam 57 integrally formed with the operating actuator 13 to set and discharge the biosensor 10.

To this end, a latch projection 65 is formed at the operating actuator 13, and a latch body 66 for engaging the latch projection 65 is provided at the body 4, and a return spring 67 for returning the operating actuator 13 to the initial position is provided.

Therefore, when the operating actuator 13 is pushed into the body 4 to its maximum, the latch projection 65 and the latch body 66 are engaged, and the operating actuator 13 is fixed. When the operating actuator 13 is further pushed into the body 4 after the test is finished, the engagement of the latch projection 65 and the latch body 66 is released, and the operating actuator 13 is returned to the initial position with the return spring 67.

When the push-in operation of the operating actuator 13 is interrupted, if the operation to return the sealing roller 43 to the sealing position is performed with the biosensor 10 halfway out of the biosensor ejecting port 26, the biosensor 10 may be trapped in between and defects of the equipment may occur. Thus, there is provided a mechanism in which the operating actuator 13 does not return to the initial position even if the push-in operation of the operating actuator 13 is interrupted.

Figure 12A:
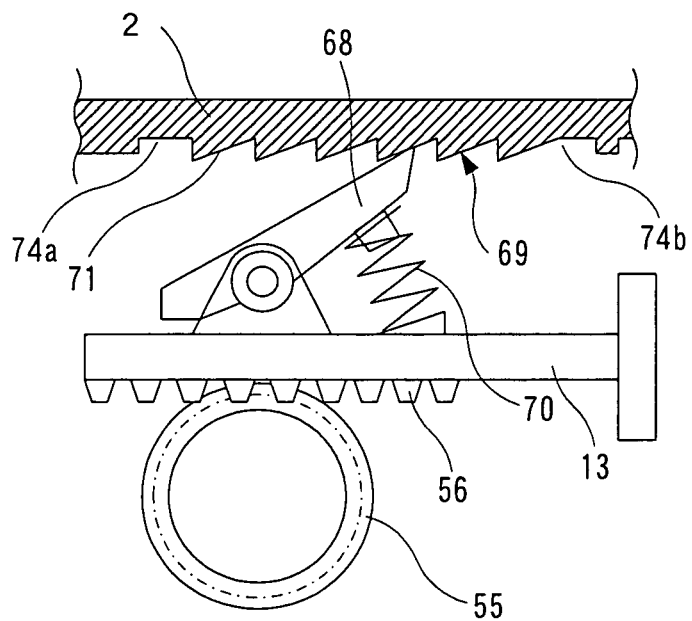
FIG. 12A is a side view of a holding mechanism for holding an operating means of the biosensor dispensing device of FIG. 1.

As shown in FIG. 12A, a nail member 68 is provided on the operating actuator 13, and a latchet 69 at where the nail member 68 is slidably movable is provided at the inner wall of the body upper case 2.

The nail member 68 is axially supported on the operating actuator 13, and is freely oscillated in the vertical direction to move closer to or away from the inner wall of the body upper case 2 and in the horizontal direction along the inner wall, and a part near the distal end thereof is coupled to the operating actuator 13 with a pressing spring 70 and is biased towards the inner wall.

Figure 12B:
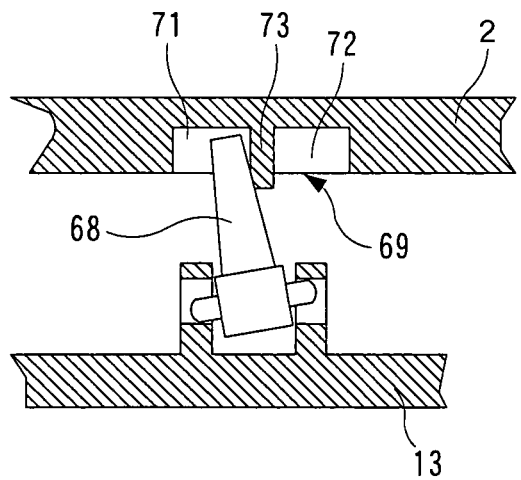
FIG. 12B is a rear view of the holding mechanism.
Figure 12C:
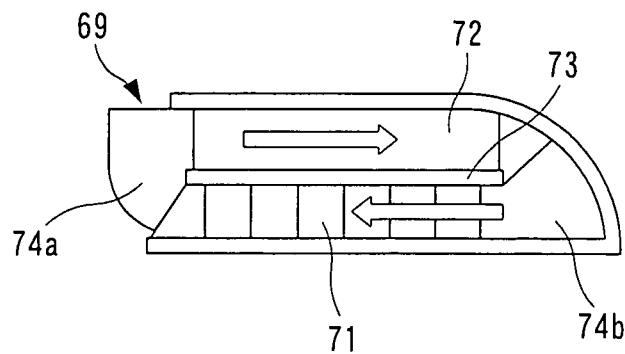
FIG. 12C is a plan view of the holding mechanism.

The latchet 69 is, as shown in FIGS. 12B and 12C, configured in an endless form with a saw-blade cam outward path 71 and a smooth homeward path 72 formed parallel to each other by way of a cam partition wall 73, and cam resting places 74*a*, 74*b* for connecting the end part of the cam outward path 71 and the end part of the cam homeward path 72 are formed.

Thus, in the outward path in which the operating actuator 13 is pushed in by a predetermined amount, the distal end of the nail member 68 is arranged in the cam outward path 71, biased upwards by the pressing spring 70 and is slidably moved over the saw-blade latchet surface. If the push-in operation of the operating actuator 13 is stopped midway, the distal end of the nail member 68 is caught at the surface of the saw-blade cam outward path 71, and the operating actuator 13 is stopped at such position.

If the operating actuator 13 is pushed in over substantially a predetermined amount, the distal end of the nail member 68 is positioned at the cam resting place 74*a*, or a turning position from the cam outward path 71 to the cam homeward path 72. At this point, with regards to the operating actuator 13, the engagement between the latch body 66 and the latch projection 65 is achieved, and the nail member 68 positioned at the cam resting place 74*a* is not caught in the returning direction of the operating actuator 13. During the returning operation of the operating actuator 13, the distal end of the nail member 68 is arranged in the cam homeward path 72 and returns to the initial position (cam resting place 74*b*) by sliding over a surface with no catching part.

A position sensor 75 for detecting that the operating actuator 13 has returned to the initial position within a fixed time, and a buzzer 76 for warning the user when no detection has been performed by the position sensor 75 are provided in the vicinity of the operating actuator 13. The warning is issued to prevent degradation of performance due to the continuous contact of the non-used biosensor 10 to air because during the time the operating actuator 13 is not returned to the initial position, the biosensor ejecting port 26 of the biosensor cartridge 6 is opened and the non-used biosensor 10 in the cartridge continuously contacts the air if the port is left opened.

More specifically, the position sensor 75 is provided at a position contacting the projection 13*a* of the operating actuator 13 when the operating actuator 13 is at the initial position, and the time from when the operating actuator 13 is pushed in at the start of measurement to when the operating actuator 13 is returned to the initial position after the measurement is finished is measured with a timing means (not shown) inside the device based on the contact/non-contact of the position sensor 75 and the projection 13*a*, and the warning is issued by the buzzer 76 when the measured value exceeds a predetermined time.

The biosensor dispensing device 1 of the first embodiment is therefore relatively compact and the user can easily carry and handle the device.

During the test, by pushing in the operating actuator 13, one of a plurality of biosensors 10 within the biosensor cartridge 6 is reliably discharged and arranged at the test position. At the same time, the non-used biosensors 10 are sealed in the cartridge 6. The used biosensor 10 is discharged from the device by further pushing in the operating actuator 13.

By manually operating the operation button 19, the information related to the test being performed can be provided, the data relating to occurrence of the biosensor 10 can be acquired, the acquired information or the stored information can be displayed on the display screen 18 or provided to other analyzing or computer apparatuses via the data port connector (not shown).

Therefore, compared to the above-mentioned conventional device loaded with the biosensor pack, in the device of the present invention, the setting operation and the discarding operation of the biosensor 10 are reliably carried out and is easy-to-use. Compared to the conventional device installed with the sensor bottle, the device of the present invention is made thinner.

Second Embodiment

A biosensor dispensing device according to a second embodiment of the present invention will now be described with reference to FIG. 13 to FIG. 18. This biosensor dispensing device is used in for example, blood-glucose measurement.

Figure 13A:
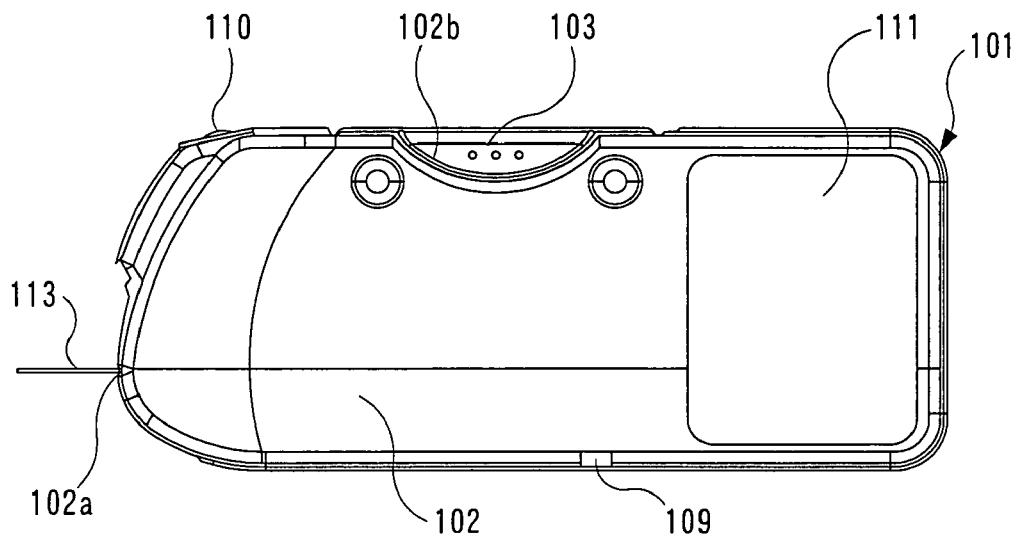
FIG. 13A is an external view of a biosensor dispensing device according to a second embodiment of the present invention.
Figure 13B:
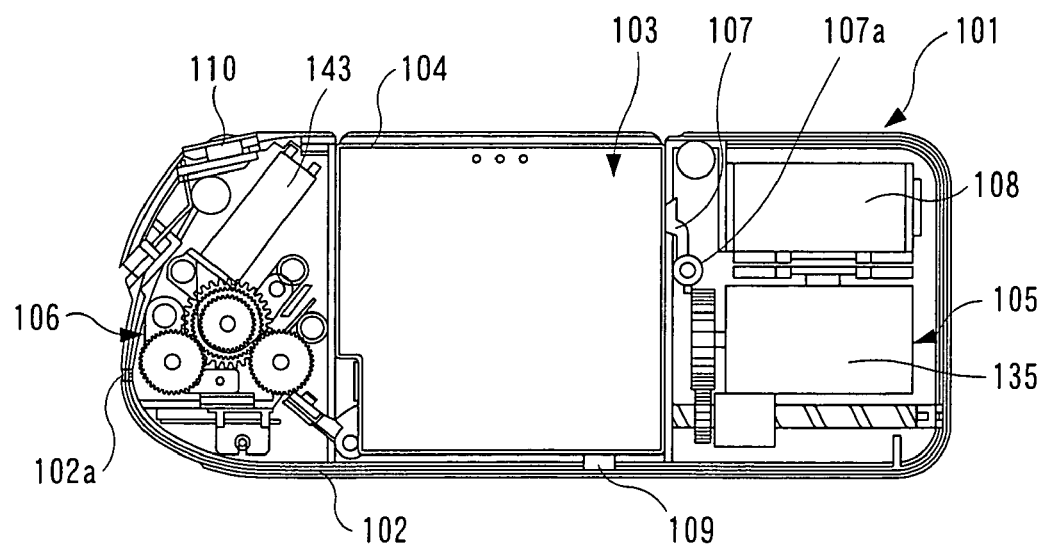
FIG. 13B is an interior view of the biosensor dispensing device according to the second embodiment of the present invention.

As shown in FIGS. 13A and 13B, the biosensor dispensing device 101 includes a cartridge storing chamber 104 for storing a biosensor cartridge 103 at a central part of a casing 102, and includes a biosensor sending out mechanism 105 and a biosensor conveying mechanism 106 on both sides of the cartridge storing chamber 104.

A lock lever 107 for fixing the biosensor cartridge 103 is provided in the vicinity of the cartridge storing chamber 104. The lock lever 107 is biased towards the cartridge storing chamber 104 with a lock lever SP 107a. Further, a control mechanism 108 including a printed wiring board on which a signal processing circuit and a control circuit for operating the biosensor sending out mechanism 105, the biosensor conveying mechanism 106 and the like are formed, a battery electrode, a battery, and a microprocessor and the like is provided.

A sensor ejecting port 102a is formed in the casing 102, and a notch 102b is formed at a portion corresponding to the cartridge storing chamber 104, through which notch 102b, the biosensor cartridge 103 is readily detachable with respect to the cartridge storing chamber 104.

A biosensor cartridge detection SW 109 for detecting the presence/absence of the biosensor cartridge 103, a set button 110 for the user to command an operation to the biosensor sending out mechanism 105, the biosensor conveying mechanism 106 and the like, and a display part 111 for displaying information such as measurement result are provided on an exterior surface of the casing 102.

As shown in FIGS. 14A and 14B, the biosensor cartridge 103 includes a sensor storing chamber 114 for storing a plurality of biosensors 113 stacked one over the other inside the cartridge case 112. Further, a sensor send-out means 116 for sending out the biosensor 113 within the sensor storing chamber 114 one by one, and discharging the relative biosensor from the sensor ejecting port 115 opened in the cartridge case 112 is built-in. A concave lock groove 112a for locking with the above-mentioned lock lever 107 is formed on the exterior surface of the cartridge case 112.

More specifically, regarding the cartridge case 112, a convex bar 112b is formed at an opposing interior surface of the case, and one region, with the convex bar 112b in between, is partitioned to the sensor storing chamber 114 and a desiccant storing chamber 117 with a partition wall 118, and a major portion of the sensor send-out means 116 is arranged in the other region.

In the sensor storing chamber 114, the biosensors 113 are stacked on the convex bar 112b each faced in the same direction, and is held down by a hold-down plate 119. The hold-down plate 119 includes a guide rib 120 slidably contacting the interior surface of the cartridge case 112 and the partition wall 118, is pressed by a spring 121, and is thus smoothly and stably movable within the biosensor storing chamber 114.

The biosensor 113 is, similar to the explanation given with reference to FIG. 3, configured by stacking a short upper layer sheet with one rounded end and a long under layer sheet with the above-mentioned one end aligned, and includes a reagent part (containing enzyme or biological sensing part) in the vicinity of the above-mentioned one end, which above-mentioned one end communicated to the reagent part with a capillary tube serves as an applying part for applying the sample, and an electrode part extending to the reagent part is provided on an exposed surface of the under layer sheet. The spring 121 is arranged at a position corresponding to a back surface of the hold-down plate 119, a position more to the left than a step 113a of the biosensor 113 and on the upper layer sheet.

The sensor send-out means 116 includes a slider 122 that slides along the interior surface of the cartridge case 112. A biosensor guide 123 for sending out the biosensor 113, and a slider guide 124 for engaging with a guide groove 112c formed along the convex bar 112b are integrally formed in the slider 122.

The slider 122 includes a convex part 122a that fits into a hole 112d formed in the cartridge case 112 while being pressed by a slider spring 125, and when a pushing shaft (hereinafter described) that fits into a concave part 122b formed at a center of the convex part 122a is not provided, the slider is pushed against the hole 112d side. Such a position of the slider 122 is hereinafter referred to as an initial position.

A slider seal ring 126 made of an elastic material such as EPDM, NBR, silicon and the like for sealing a space formed with the cartridge case 112 when the slider 122 is at the initial position 122 is attached to the convex part 122a.

A seal plate 127 for opening and closing the sensor ejecting port 115 is attached exterior to the cartridge case 112. The seal plate 127 is freely rotatable about a supporting shaft 127a and is pushed by a seal plate spring 128 to close the sensor ejecting port 115 when the slider 122 is at the initial position.

Figure 15A:
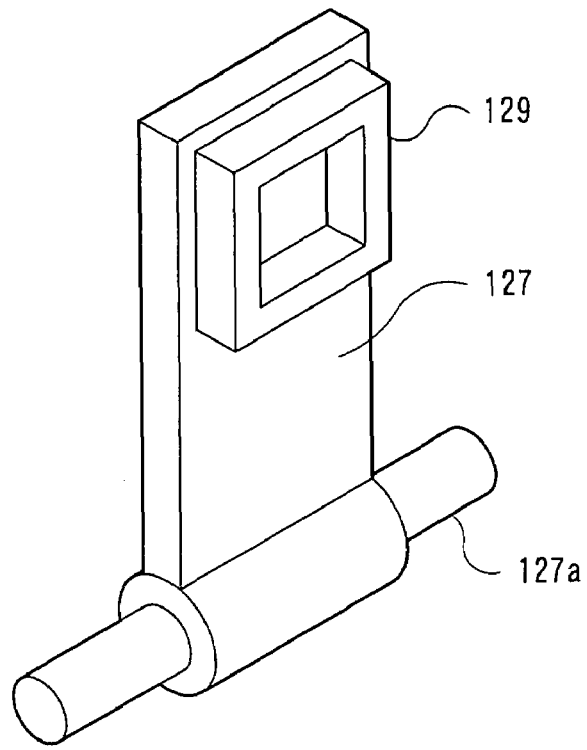
FIG. 15A is a perspective view of a sealing plate provided in the biosensor cartridge of FIG. 14.

As shown in FIG. 15A, a seal ring 129 made of an elastic material such as EPDM, NBR, silicon and the like pressure welded to the exterior surface of the cartridge case 112 around the sensor ejecting port 115 is attached to the seal plate 127. A small projection 112e for enhancing the sealability of the seal ring 129 is formed on the exterior surface of the cartridge case 112 around the sensor ejecting port 115. It is to be noted that the seal ring 129 may also be attached on the cartridge case 112 side.

Figure 15B:
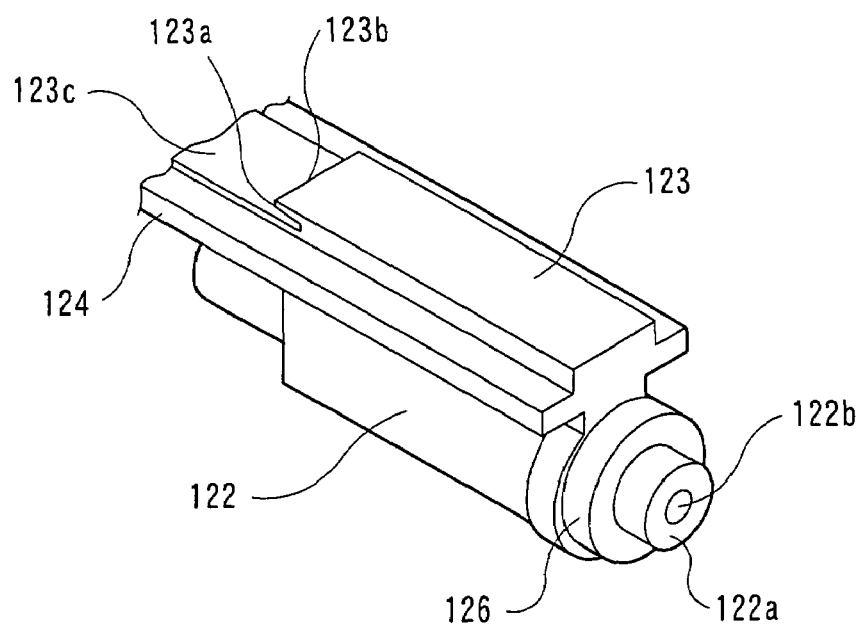
FIG. 15B is a partial perspective view of a slider member provided in the biosensor cartridge of FIG. 14.

As also shown in FIG. 15B, the biosensor guide 123 integrally formed with the slider 122 is configured with an upper guide 123b and a lower guide 123c formed in a step-form so as to include a slit 123a. The dimension of the biosensor guide 123 is such that when the slider 122 is at the initial position, a distal end of the lower guide 123c is positioned in the vicinity of the biosensor ejecting port 115, the biosensor 113 is arranged on the lower guide 123c more inward than the distal end, and the slit 123a of the upper guide 123b is faced against the rear end of the under layer sheet of the biosensor 113 at the bottom layer. Thus, when discharging the biosensor 113, the upper guide 123b holds the under layer sheet of the biosensor 113 in the slit 123a and reliably pushes the biosensor, and the lower guide 123c protects the front end of the biosensor 113.

In the desiccant storing chamber 117, by arranging a divider 130 in multi-stages, a meandering air flow path 131 connecting to an opening 118a communicated to the biosensor storing chamber 114 is formed and desiccants 132 are filled in the air flow path 131. The desiccant 132 is molded and housed in a preferable shape that corresponds to the shape of the desiccant storing chamber 117, that is, to a granular having an outer diameter corresponding to the width of the air flow path 131.

The desiccant 132 is provided to absorb the moisture within the cartridge case 112 and maintain each biosensor 113 in a dry state. The moisture absorption capability of the desiccant 132 is normally high in the initial stage and then gradually saturates, and thus by storing the desiccants 132 along the meandering air flow path 131, the drying capability is exhibited sequentially from the desiccant 132 located at the inflow end of the air flow path 131 to the desiccant 132 located at the outflow end, and the drying capability can be effectively exhibited over a long period of time. Further, by having the shape of the desiccant 132 correspond to the shape of the desiccant storing chamber 117, the space of the desiccant storing chamber 117 can be effectively used, and handling of the desiccant 132 of when assembling the biosensor cartridge 103 becomes facilitated.

As described above, the biosensor cartridge 103 suitably stores the desiccant 132 and when the biosensor 113 is not being discharged, the sensor ejecting port 115 and the hole 112d of the cartridge case 112 are sealed, thus blocking the inside of the cartridge case 112 from outside air. Thus, degradation in the performance of the biosensor 113 due to moisture can be suppressed. This effect is obtained irrespective of whether the biosensor cartridge 103 is installed in the biosensor dispensing device 101 or is removed from the biosensor dispensing device 101.

Figure 16A:
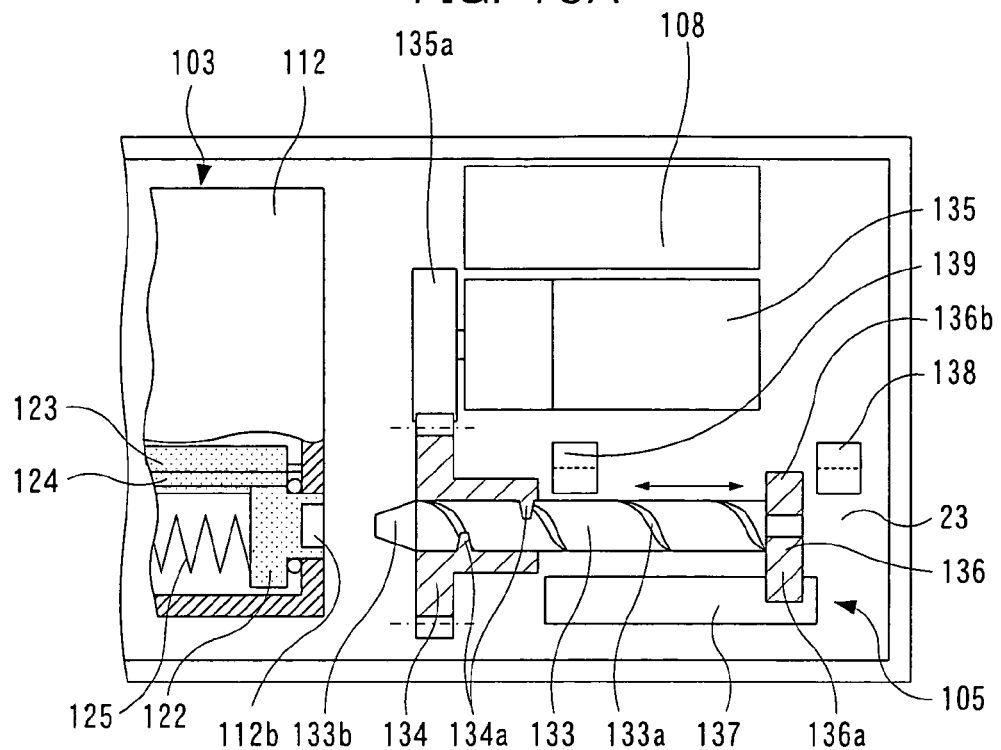
FIG. 16A is a partial sectional view illustrating a first state of operation of a sensor sending out mechanism of the biosensor dispensing device of FIG. 13.
Figure 16B:
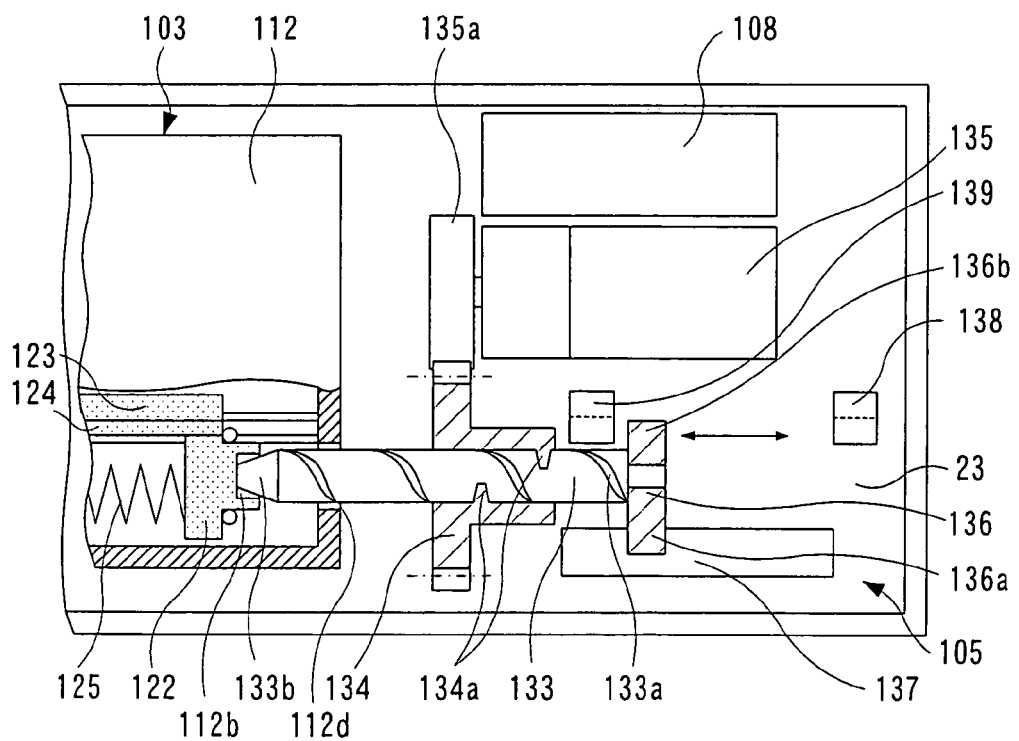
FIG. 16B is a partial sectional view illustrating a second state of operation of a sensor sending out mechanism of the biosensor dispensing device of FIG. 13.

FIGS. 16A and 16B show the biosensor sending out mechanism 105 for sending out the biosensor 113 from the biosensor cartridge 103.

The biosensor sending out mechanism 105 includes a sensor pushing shaft 113 and a shaft driving motor 135 for driving the sensor pushing shaft 133 through a shaft gear 134. A bottom case 102a forms the casing 102 in combination with a top case.

More specifically, the sensor pushing shaft 133 includes a spiral groove 133a formed on an outer periphery surface thereof so as to encircle the shaft center, and a tapered distal end 133b that fits into the concave part 122b of the slider 122 within the biosensor cartridge 103, and is inserted through the shaft gear 134 formed with a pin 134a that slidably engages the spiral groove 133a.

The shaft driving motor 135 gears with the shaft gear 134 with a motor gear 135a attached to the shaft of the shaft driving motor 135, and the reciprocal rotation of the shaft gear 134 causes the sensor pushing shaft 133 to exit, thus sliding the slider 122.

A shaft regulating knob 136 including a regulating rib 136a and a blocking rib 136b is attached to the rear end of the sensor pushing shaft 133.

A regulating rib guide 137 is arranged facing the bottom case 102a and the top case so as to sandwich the regulating rib 136a, and performs rotation regulation of the sensor pushing shaft 133 and guiding during the sliding operation.

Position detection sensors 138 and 139 each includes a light-emitting photosensor and a light-receiving photosensor interior to a slit through where the blocking rib 136b passes, and is arranged with a distance in between along the sensor pushing shaft 133, and with regards to the sensor pushing shaft 133, detects a home position at where the blocking rib 136b enters the position detection sensor 138 and a push-out position at where the blocking rib 136b enters the position detection sensor 139.

Figure 17A:
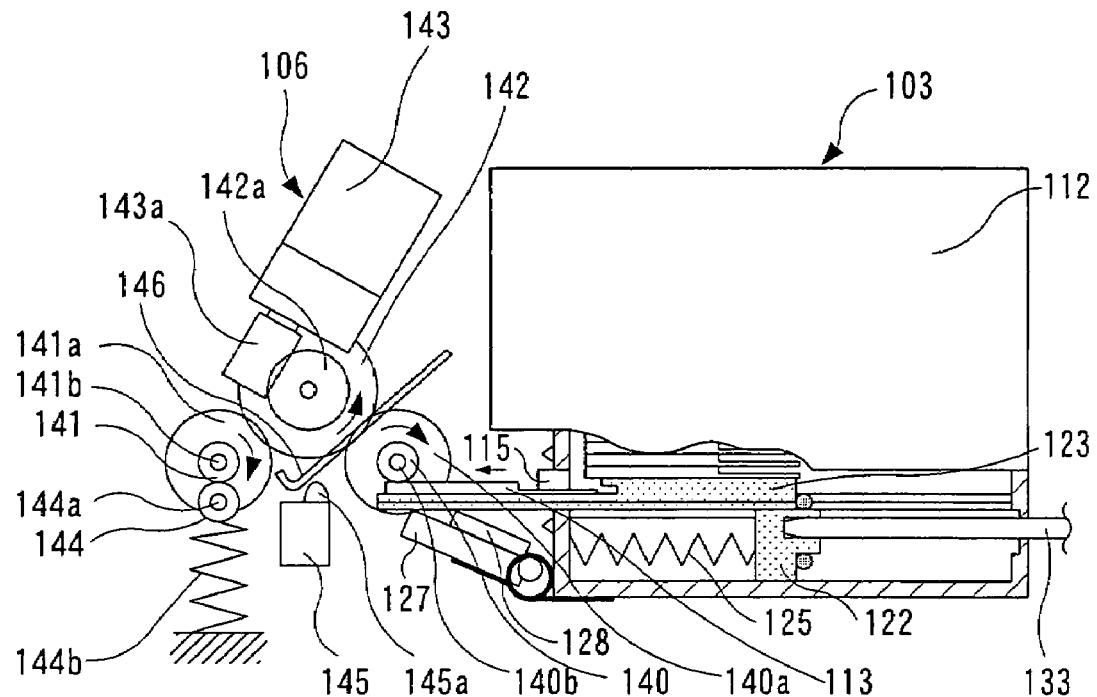
FIG. 17A is a partial sectional view illustrating a first state of operation of a sensor conveying mechanism of the biosensor dispensing device of FIG. 13.
Figure 17B:
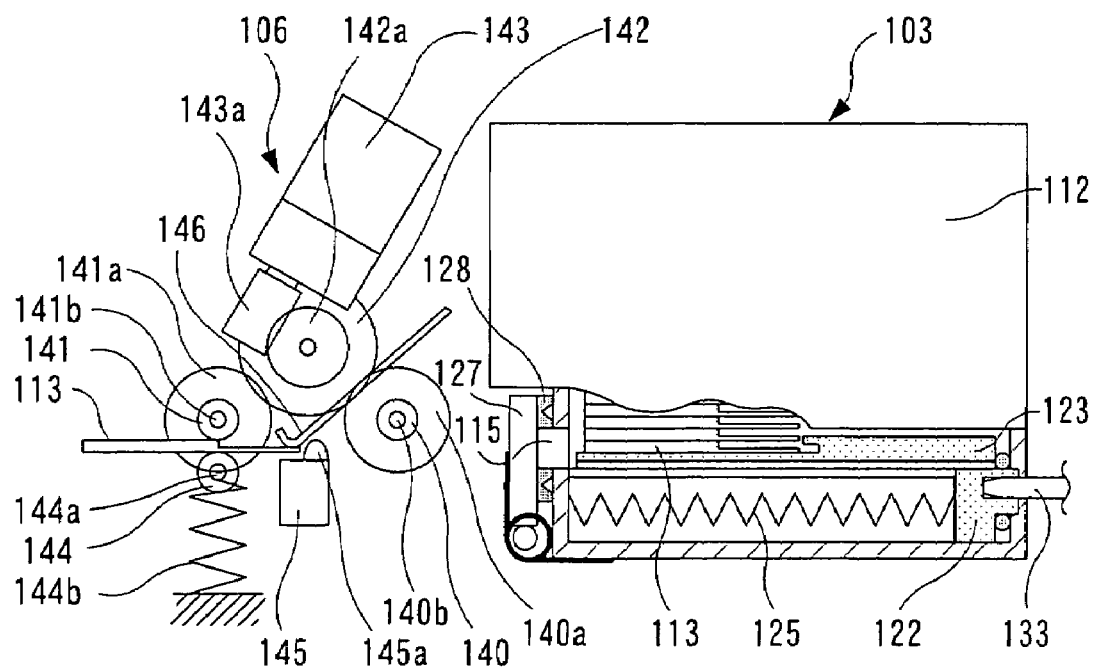
FIG. 17B is a partial sectional view illustrating a second state of operation of a sensor conveying mechanism of the biosensor dispensing device of FIG. 13.

FIGS. 17A and 17B show a conveying mechanism 106 for conveying the biosensor 113 discharged from the biosensor cartridge 103 to a predetermined test position.

The conveying mechanism 106 includes conveying rollers 140, 141 for conveying the biosensor 113, and a conveying motor 143 for rotating the conveying rollers 140, 141 through a reduction gear 142 of two-stage gear configuration. The conveying motor 143 gears with a worm wheel 142a of the reduction gear 142 with a worm 143a.

The conveying roller 140 is made of an elastic material, is attached to a conveying roller shaft 140b with a conveying roller gear 140a geared with the reduction gear 142, is arranged in the vicinity of the sensor ejecting port 115, is rotated by the conveying motor 143 and the reduction gear 142, and sandwiches and sends out the biosensor 113 discharged from the sensor ejecting port 115 with the biosensor guide 123 of the slider pressed by the seal plate 127.

The conveying roller 141 is made of an elastic material, is attached to a conveying roller shaft 141b with the conveying roller gear 141a geared with the reduction gear 142, and is arranged in the vicinity of the conveying roller 140. A driven roller 144 attached to a driven roller shaft 144a is pushed against the conveying roller 141 by a driven roller compressing spring 144b. Thus, the conveying roller 141 is rotated by the conveying motor 143 and the reduction gear 142, and sandwiches and discharges the biosensor 113 sent out by the conveying roller 140 with the driven roller 144.

A biosensor detection SW 145 for detecting the position of the biosensor 113 is arranged along the conveying path from the conveying roller 140 to the conveying roller 141. The biosensor detection SW 145 includes a turnable detection knob 145a, and is switched when the biosensor 113 starts sliding over the detection knob 145a and when the biosensor 113 finishes sliding. An electrode arm 146 for contacting the electrode part of the biosensor 113 and transmitting the electrical signal to the electrical circuit is also arranged on the conveying path.

Figure 18:
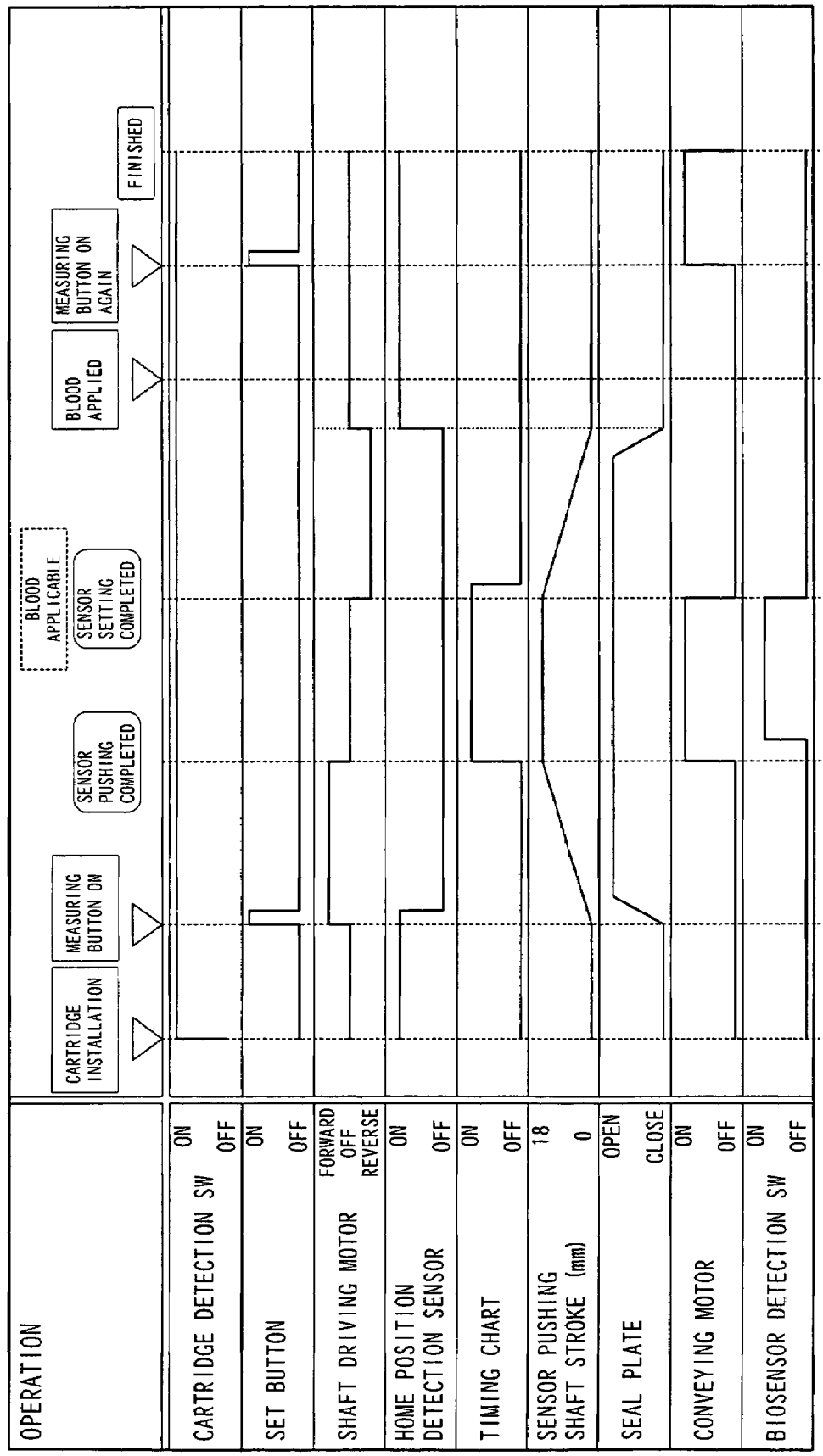
FIG. 18 is a timing chart of the biosensor dispensing device of FIG. 13.
Figure 20A:
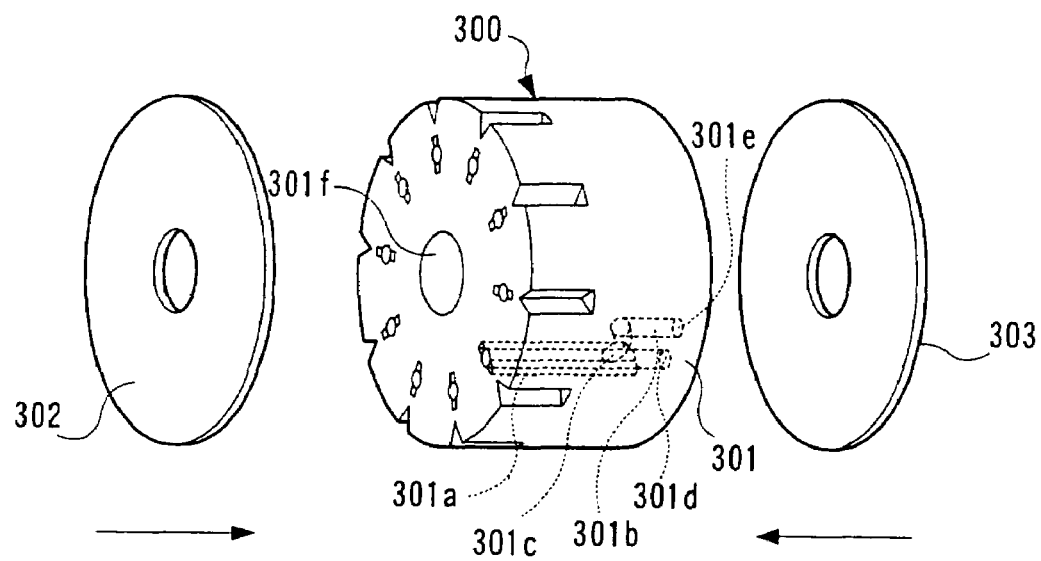
FIG. 20A is an exploded perspective view of a sensor bottle of the conventional biosensor dispensing device.
Figure 20B:
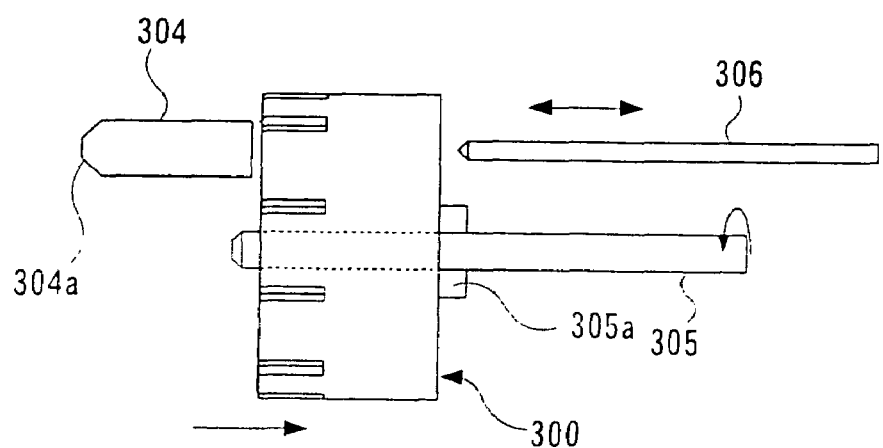
FIG. 20B is a partial side view of the conventional biosensor dispensing device.

A sequence of operations of the biosensor dispensing device 101 and the biosensor cartridge 103 will now be described with further reference to a timing chart of FIG. 18.

When the biosensor dispensing device 101 is not operated, the sensor pushing shaft 133 is stopped at the home position, and thus has no influence on the detachment of the biosensor cartridge 103.

When the biosensor cartridge 103 is installed in the cartridge storing chamber 104, the lock lever 107 enters the lock groove 112a of the cartridge case 112 and locks the biosensor cartridge 103, while the biosensor cartridge detection SW 109 detects the presence of the biosensor cartridge 103 and measurement becomes possible.

When the set button 110 is turned ON, the shaft driving motor 135 rotates in the counterclockwise direction when seen from the output shaft, thus rotating the shaft gear 134 in the clockwise direction, and advances the sensor pushing shaft 133 towards the biosensor cartridge 133.

The sensor pushing shaft 133 slides the slider 122 against the slider spring 125, and the sensor lower guide 123c integrated with the slider 122 pushes the seal plate 127 and opens the biosensor ejecting port 115, while the sensor upper guide 123b pushes the biosensor 113 out of the biosensor ejecting port 115.

After the sensor pushing shaft 133 reaches the push-out position, the shaft driving motor 135 is stopped, and the sensor pushing shaft 133 and the slider 122 also come to a rest. The push-out position is set at a position at where the front end of the biosensor 113 projected out of the biosensor ejecting port 115 by the sensor pushing shaft 133 and the slider 122 overlaps the conveying roller 140. Thus, the pushed out biosensor 113 is held between the seal plate 127 pushed by the seal plate spring 128 and the conveying roller 140 while bearing on the lower guide 123c.

With the stopping of the shaft driving motor 135, the conveying motor 143 is activated, the reduction gear 142 is rotated in the counterclockwise direction, and the conveying roller 140 and the conveying roller 141 are rotated in the clockwise direction, thus conveying the biosensor 113. The conveying motor 143 may be activated at the start of driving the shaft driving motor 135 or after a slight time delay. After the biosensor 113 passes over the detection knob 145a of the biosensor detection SW 145, the conveying motor 143 is stopped.

As a result, the biosensor 113 is sandwiched between the conveying roller 141 and the driven roller 144, and the applying part at the front end is arranged at a predetermined test position exposed from the sensor ejecting port 102a of the casing 102. Further, the electrode arm 146 electrically contacts the electrode pattern of the biosensor 113 and measurement becomes possible.

On the other hand, after the finish of passing of the biosensor 113 is detected by the biosensor detection SW 145, the shaft driving motor 135 is counter-rotated, thus backing the sensor pushing shaft 133, and at the time the pushing shaft 133 reaches the home position, the shaft driving motor 135 is stopped and the sensor pushing shaft 133 comes to a rest.

Further, the slider 122, pushed by the sensor pushing shaft 133, returns to the initial position by the slider spring 125, and the slider seal ring 126 seals between the slider 122 and the cartridge case 112.

The seal plate 127 pushed by the slider 122 is turned by the seal plate spring 128 and closes the sensor ejecting port 115, and the seal ring 129 attached to the seal plate 127 seals between the seal plate 127 and the cartridge case 112.

When blood is applied to the applying part of the biosensor 113 arranged at the test position, the blood is drawn to the reagent part through the capillary tube, the blood-glucose or a measuring object component chemically reacts with the reagent, and the electrical signal corresponding to the blood-glucose level is sent to the signal processing circuit through the electrode pattern and the electrode arm 146. When set by the user, the information is displayed on the display part 111.

When the set button 110 is turned ON again after the measurement is finished, the conveying motor 143 is activated, thus rotating the reduction gear 142 in the counter-clockwise direction, thereby rotating the conveying roller 141 in the clockwise direction and the biosensor 113 sandwiched between the conveying roller 141 and the driven roller 144 is further conveyed and is discharged out of the casing 102.

As described above, the biosensor dispensing device 101 of the second embodiment has a simple configuration with the biosensor cartridge storing chamber 104, the biosensor sending out mechanism 105, and the biosensor conveying mechanism 106 lined in a straight line, and is relatively compact, and thus the user can easily carry and handle the device.

With regards to the test, with the biosensor cartridge 103 installed, the biosensor 113 is set to the test position one by one with a simple operation, and after the test is finished, is discharged out of the device.

Further, information related to the test being performed may be given, data for occurrence of the biosensor 113 may be acquired, and the acquired information or the stored information may be displayed on the display part 111, or may be supplied to other analyzing or computer apparatuses via the data port connector (not shown).

The biosensor cartridge 103 stores a great number of biosensors 113 along with the desiccants 132 and the like, and alone ensures sealability, and thus has high reliability, is easily handled, and is made thinner.

Therefore, compared to the above-mentioned conventional device loaded with the biosensor pack, the setting operation and the discarding operation of the biosensor 10 are reliably performed and the device is more easy to use. Further, compared to the conventional device installed with the sensor bottle, the device is made thinner.

It is to be noted that the first embodiment and the second embodiment described herein are only illustrative and should not limit the scope of the invention. For example, the biosensor dispensing devices 1, 101 may also be used, in addition to the above-mentioned blood-glucose test, in testing various types of fluid that can be analyzed using the reagent material.

INDUSTRIAL APPLICABILITY

As described above, the biosensor cartridge of the present invention is a type in which the biosensors are stacked one over the-other, and thus a great number of biosensors can be stored therein, but can still be made compact and be easily handled. Further, since sealability and moisture-proof effect are high, even if a certain number of days are required to consume all the biosensors, the performance thereof is not degraded and the reliability is high.

Further, the biosensor dispensing device of the present invention installs the biosensor cartridge therein, and in cooperation with the biosensor cartridge, sets the biosensor in a test state one by one with a simple operation, and discharges the biosensor out of the device after the test is finished. A thinner and a smaller device complying with the biosensor cartridge is obtained.

The invention claimed is:

1. A biosensor dispensing device comprising:
   a biosensor cartridge for storing a stacked plurality of biosensors, the biosensor cartridge comprising:
      a sensor ejecting port;
      a sensor ejecting means for ejecting a biosensor from the biosensor cartridge via the sensor ejecting port, the sensor ejecting means located in the biosensor cartridge, the sensor ejecting port located in a wall of the biosensor cartridge facing tips of the biosensors, wherein the sensor ejecting port is closed except when the biosensors are being ejected;
   a biosensor dispensing device body comprising:
      a cartridge storing chamber for detachably holding the biosensor cartridge;
      a sensor sending out mechanism for driving the sensor ejecting means in the biosensor cartridge;
      a sensor conveying mechanism for conveying an ejected biosensor from the sensor ejecting port to a predetermined test position; and
      an operating part outside the device body, for the operating the sensor sending out mechanism, thereby ejecting a biosensor from the sensor ejecting port,
      wherein the biosensor ejecting means comprises a sliding member for pushing a rear end of a stacked biosensor, and
      the sensor sending out mechanism comprises a pushing member for pushing and sliding the sliding member.

2. The biosensor dispensing device according to claim 1, further comprising sensor conducting means for connecting electrodes on a biosensor in such test position, and for transmitting electrical data from such biosensor to an electrical circuit within the device body.

3. The biosensor dispensing device according to claim 2, further comprising a display unit on an exterior surface of the device body for receiving electrical data from the electrical circuit corresponding to such electrical data from the biosensor, and for displaying the data from the electrical circuit.

4. The biosensor dispensing device according to claim 1, wherein the operating part is moveable into the device body, such that when the operating part is moved into the device body, the biosensor is ejected from the cartridge, conveyed to the test position and electrically connected to an electrical circuit within the device body, thereby entering a test state.

5. The biosensor dispensing device according to claim 4, wherein a power source of the body is driven when the biosensor is in the test position.

6. The biosensor dispensing device according to claim 4, wherein the biosensor is ejected out of the device body after the operating part is moved into the device body.

7. The biosensor dispensing device according to claim 1, wherein the operating part is for electrically operating the sensor sending out mechanism.

8. The biosensor dispensing device according to claim 7, wherein the biosensor cartridge includes a seal plate for opening the sensor ejecting port only when ejecting a biosensor and closing such sensor ejecting port once such biosensor has been ejected.

9. The biosensor dispensing device according to claim 7, wherein the pushing member of the sensor sending out mechanism is biased towards the sliding member of the biosensor cartridge and includes detection means for detecting an operation stroke of the pushing member.

10. The biosensor dispensing device according to claim 7, further comprising detection means for detecting a position of a biosensor in such test position.

11. The biosensor dispensing device according to claim 7, wherein the sensor sending out mechanism and the sensor conveying mechanism are independently operable.

12. A biosensor dispensing device comprising:

A biosensor dispensing device comprising:

a biosensor cartridge for storing a stacked plurality of biosensors, the biosensor cartridge comprising;

a sensor ejecting port;

a sensor ejecting means for ejecting a biosensor from the biosensor cartridge via the sensor ejecting port, the sensor ejecting means located in the biosensor cartridge, the sensor ejecting port located in a wall of the biosensor cartridge facing tips of the biosensors, wherein the sensor ejecting port is closed except when the biosensors are being ejected;

a biosensor dispensing device body comprising;

a cartridge storing chamber for detachably holding the biosensor cartridge;

a sensor sending out mechanism for driving the sensor ejecting means in the biosensor cartridge;

a sensor conveying mechanism for conveying an ejected biosensor from the sensor ejecting port to a predetermined test position; and an operating part outside the device body, for the operating the sensor sending out mechanism, thereby ejecting a biosensor from the sensor ejecting port, wherein the sensor ejecting means for the biosensor cartridge comprise a cylindrical rotating member and a sliding member that slides with a rotation of the rotating member, such that when the rotating member rotates, the sliding member to pushes a rear end of a biosensor, the sensor sending out mechanism includes a rotating means for rotating the cylindrical rotating member of the biosensor cartridge, and the operating part is movable into the device body with a forefinger of a hand gripping a bottom portion of an outside surface of the device body.

13. The biosensor dispensing device according to claim 12, wherein the operating part is biased to exit the device body, and the operating part is movable into the device body, to actuate the driving mechanism.

14. The biosensor dispensing device according to claim 13, wherein the sensor sending out mechanism drives the sensor ejecting means which ejects a biosensor in a direction opposite a direction of pushing the operating part into the device body to actuate the sensor sending out mechanism.

15. The biosensor dispensing device according to claim 12, further comprising valve means for opening and closing the sensor ejecting port for the biosensor cartridge.

16. The biosensor dispensing device according to claim 15, wherein the valve means is a roller rolling over an exterior surface of the biosensor cartridge.

17. The biosensor dispensing device according to claim 15, further comprising sensor conducting means, wherein the sensor conducting means and the valve means are gear-coupled to the sensor sending out mechanism.

18. The biosensor dispensing device according to claim 17, wherein the sensor conducting means are for connecting to electrodes on a biosensor in the test position, and for transmitting electrical data from such a biosensor to an electrical circuit within the device body, and connecting members, supported by the device body, connect at one end to the sensor conducting means and the valve means, respectively, and connect at the other end to a cam on the operating part, said cam for holding and turning the other end of each connecting member.

19. The biosensor dispensing device according to claim 12, further comprising a cartridge holding mechanism for securing the biosensor cartridge when the operating part is not fully extended outside the device body.

20. The biosensor dispensing device according to claim 19, wherein the cartridge holding mechanism is gear-coupled to the operating part.

21. The biosensor dispensing device according to claim 13, further comprising detection means for detecting a return of the operating part to a fully extended position outside the device body.

22. The biosensor dispensing device according to claim 21, wherein the detection means detect a contact with a member of the operating part.

23. The biosensor dispensing device according to claim 12, wherein the sensor sending out mechanism includes connection switching means for connecting or releasing connection of the sensor sending out mechanism with the sensor ejection means corresponding to a closed or open state, respectively, of a lid body of the cartridge storing chamber.

24. The biosensor dispensing device according to claim 12, further comprising:

a nail member on the operating part, said nail member having a distal end that is able to oscillate;

a sliding path in an inner wall of the device body, for receiving the distal end of the nail member, and a saw-blade concavo-convex part for locking the distal end of the nail member and for fixing the operating part in position when the operating part is stopped on the sliding path.

25. The biosensor dispensing device according to claim 24, wherein the sliding part is configured in a loop-form comprising an outward path on which the distal end of the nail member slides when the operating part is moved into the device body and a homeward path on which the distal end of the nail member slides when the operating part is extended outside the device body, and the saw-blade concavo-convex part is located on the outward path.

26. The biosensor dispensing device according to claim 12, further comprising a latch mechanism for locking the operating part in place when the biosensor is in such test position.

27. The biosensor dispensing device according to claim 26, wherein the latch mechanism comprises a latch projection on the operating part and a latch body part in the device body for locking the latch projection.

* * * * *